(12) United States Patent
Gutterer

(10) Patent No.: US 6,476,025 B1
(45) Date of Patent: Nov. 5, 2002

(54) PHENYLPHENNANTHRIDINES WITH PDE-IV INHIBITING ACTIVITY

(75) Inventor: Beate Gutterer, Allensbach (DE)

(73) Assignee: Altana Pharma AG, Konstanz (DE)

( * ) Notice: Subject to any disclaimer, the term of this patent is extended or adjusted under 35 U.S.C. 154(b) by 0 days.

(21) Appl. No.: 09/889,144

(22) PCT Filed: Jan. 12, 2000

(86) PCT No.: PCT/EP00/00172

§ 371 (c)(1),
(2), (4) Date: Jul. 12, 2001

(87) PCT Pub. No.: WO00/42020

PCT Pub. Date: Jul. 20, 2000

(30) Foreign Application Priority Data

Jan. 15, 1999 (EP) .............................. 99100694

(51) Int. Cl.⁷ ................. A61K 31/4738; C07D 221/12; C07D 401/10; C07D 403/10; A61P 11/00
(52) U.S. Cl. .............................. 514/232.8; 514/217.07; 514/253.8; 514/287; 514/289; 514/290; 514/298; 540/597; 544/126; 544/361; 546/65; 546/74; 546/108; 546/109
(58) Field of Search ................................. 546/109, 108, 546/65, 74; 574/298, 287, 289, 290; 544/126, 361; 514/232.8, 253.03, 217.07; 540/597

(56) References Cited

U.S. PATENT DOCUMENTS 3,899,494 A  8/1975  Ott et al.
6,008,215 A  12/1999 Flockerzi
6,121,279 A  9/2000  Gutterer
6,127,378 A  10/2000 Gutterer
6,143,759 A  11/2000 Flockerzi
6,191,138 B1 2/2001  Gutterer

FOREIGN PATENT DOCUMENTS

WO  WO 98/55481  12/1998
WO  WO 99/05111  2/1999

*Primary Examiner*—Evelyn Mei Huang
(74) *Attorney, Agent, or Firm*—Nath & Associates PLLC; Todd L. Juneau; Joshua B. Goldberg

(57) ABSTRACT

Compounds of formula (I), in which R1, R2, R3, R31, R4, R5, R51, R6, R13 and R20 have the meaning indicated in the description, are novel active bronchial therapeutics

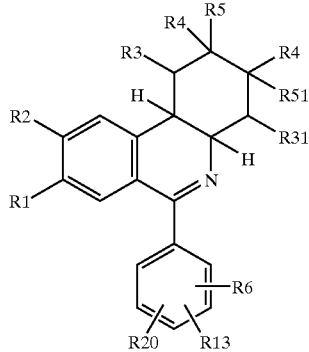

10 Claims, No Drawings

PHENYLPHENNANTHRIDINES WITH PDE-IV INHIBITING ACTIVITY

This application is a 371 of PCT/EP00/00172, filed on Jan. 12, 2000.

FIELD OF APPLICATION OF THE INVENTION

The invention relates to novel 6-phenylphenanthridines, which are used in the pharmaceutical industry for the production of medicaments.

KNOWN TECHNICAL BACKGROUND

Chem. Ber. 1939, 72, 675–677, J. Chem. Soc., 1956, 4280–4283 and J. Chem. Soc.(C), 1971, 1805 describe the synthesis of 6-phenylphenanthridines. The International Applications WO 97/28131 and WO 97/35854 describe 6-phenyl- and 6-pyridylphenanthridines as PDE4 inhibitors.

DESCRIPTION OF THE INVENTION

It has now been found that the novel 6-phenylphenanthridines described in greater detail below differ from the previously known 6-phenylphenanthridines by a different substitution pattern on the 6-phenyl ring and have surprising and particularly advantageous properties.

The invention thus relates to compounds of the formula I,

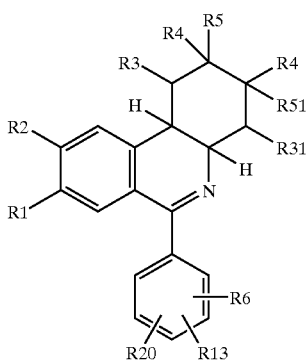

(I)

in which

R1 is hydroxyl, 1–4C-alkoxy, 3–7C-cycloalkoxy, 3–7C-cycloalkylmethoxy or completely or predominantly fluorine-substituted 1–4C-alkoxy, R2 is hydroxyl, 1–4C-alkoxy, 3–7C-cycloalkoxy, 3–7C-cycloalkylmethoxy or completely or predominantly fluorine-substituted 1–4C-alkoxy, or in which R1 and R2 together are a 1–2C-alkylenedioxy group, R3 is hydrogen or 1–4C-alkyl, R31 is hydrogen or 1–4C-alkyl, or in which R3 and R31 together are a 1–4C-alkylene group, R4 is hydrogen or 1–4C-alkyl, R5 is hydrogen, R51 is hydrogen, or in which R5 and R51 together represent an additional bond, R6 is O—R7, S—R8, C(O)—R9, CH$_2$—R10, S(O)$_2$-aryl, O—S(O)$_2$—R11, pyrrolidin-1-yl, pyrrolidin-1-yl-2-one, pyrrolidin-1-yl-2,5-dione, piperidin-1-yl, piperidin-1-yl-2-one or piperidin-1-yl-2,6-dione, where R7 is 3–7C-cycloalkyl, 3–7C-cycloalkylmethyl, 1–4C-alkoxy-1–4C-alkyl, aryl or phenyl-1–4C-alkyl, R8 is hydrogen, 1–4C-alkyl, 1–4C-alkylcarbonyl, arylcarbonyl, trifluoromethyl, difluoromethyl, trichloromethyl or phenyl, R9 is 1–4C-alkyl, 3–7C-cycloalkyl, 3–7C-cycloalkylmethyl, 1-pyrrolidinyl, 1-piperidinyl, 1-piperazinyl, 4-methylpiperazinyl, 4-morpholinyl or aryl, R10 is hydroxyl, halogen, cyano, carboxyl, 1–4C-alkoxy, phenoxy, 1–4C-alkoxycarbonyl, aminocarbonyl, mono- or di-1–4C-alkylaminocarbonyl, N(R15)R16 or 1–4C-alkylcarbonylamino, and R11 is 1–4C-alkyl, amino, mono- or di-1–4C-alkylamino or aryl, aryl is phenyl, pyridyl or R12-substituted phenyl, where R12 is hydroxyl, halogen, carboxyl, nitro, amino, cyano, 1–4C-alkyl, trifluoromethyl, 1–4C-alkoxy, 1–4C-alkoxycarbonyl, 1–4C-alkylcarbonylamino, 1–4C-alkylcarbonyloxy or aminocarbonyl, R13 is hydrogen, hydroxyl, halogen, cyano, nitro, amino, 1–4C-alkyl, trifluoromethyl, 1–4C-alkoxy, completely or predominantly fluorine-substituted 1–4C-alkoxy, phenyl, phenyl-1–4C-alkyl, C(O)—OR14, C(O)—N(R15)R16, N(R17)R18, S(O)$_2$—R19, S(O)$_2$—N(R15)R16 or has one of the meanings of R6, where R14 is hydrogen, 1–4C-alkyl, 3–7C-cycloalkyl or 3–7C-cycloalkylmethyl, R15 is hydrogen, 1–4C-alkyl, 3–7C-cycloalkyl or 3–7C-cycloalkylmethyl, R16 is hydrogen, 1–4C-alkyl, 3–7C-cycloalkyl, 3–7C-cycloalkylmethyl or aryl, or where R15 and R16, together and including the nitrogen atom to which both are bonded, represent a 1-pyrrolidinyl, 1-piperidinyl, 1-piperazinyl, 4-methylpiperazin-1-yl, 1-hexahydroazepinyl or 4-morpholinyl radical, R17 is hydrogen, 1–4C-alkyl, S(O)$_2$—R19 or S(O)$_2$-aryl, R18 is 1–4C-alkyl, 1–4C-alkylcarbonyl, 3–7C-cycloalkylcarbonyl, 3–7C-cycloalkylmethylcarbonyl, S(O)$_2$—R19 or S(O)$_2$-aryl, and R19 is 1–4C-alkyl, R20 is hydrogen, hydroxyl, halogen, nitro, amino, 1–4C-alkyl, trifluoromethyl, 1–4C-alkoxy, completely or predominantly fluorine-substituted 1–4C-alkoxy, 3–7C-cycloalkoxy, 3–7C-cycloalkylmethoxy, CH$_2$-R10, carboxyl, 1–4C-alkoxycarbonyl, 1–4C-alkylcarbonyloxy, 1–4C-alkylcarbonylamino or aminocarbonyl, and the salts, the N-oxides and the salts of the N-oxides of these compounds.

1–4C-Alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

3–7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As completely or predominantly fluorine-substituted 1–4C-alkoxy, for example, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals may be mentioned. "Predominantly" in this connection means that more than half of the hydrogen atoms are replaced by fluorine atoms.

1–2C-Alkylenedioxy represents, for example, the methylenedioxy [—O—CH$_2$—O—] and the ethylenedioxy [—O—CH$_2$—CH$_2$—O—] radicals.

If R3 and R31 together have the meaning 1–4C-alkylene, the positions 1 and 4 in compounds of the formula I are linked to one another by a 1–4C-alkylene bridge, 1–4C-alkylene representing straight-chain or branched alkylene radicals having 1 to 4 carbon atoms. Examples which may be mentioned are the radicals methylene [—CH$_2$—], ethylene [—CH$_2$—CH$_2$—], trimethylene [—CH$_2$—CH$_2$—CH$_2$—], 1,2dimethylethylene [—CH(CH$_3$)—CH(CH$_3$)—] and isopropylidene [—C(CH$_3$)$_2$—].

If R5 and R51 together are an additional bond, then the carbon atoms in positions 2 and 3 in compounds of the formula I are linked to one another via a double bond.

Halogen within the meaning of the invention is bromine, chlorine or fluorine.

3–7C-Cycloalkyl represents cyclopropyl, cyclobutyl, cyclopentyl, cyclohexyl and cycloheptyl, of which cyclopropyl, cyclobutyl and cyclopentyl are preferred.

3–7C-Cycloalkylmethyl represents a methyl radical which is substituted by one of the abovementioned 3–7C-cycloalkyl radicals. Preferably, the 3–5C-cycloalkylmethyl radicals cyclopropylmethyl, cyclobutylmethyl and cyclopentylmethyl may be mentioned.

1–4C-Alkoxy-1–4C-alkyl represents one of the abovementioned 1–4C-alkyl radicals, which is substituted by one of the abovementioned 1–4C-alkoxy radicals. Examples which may be mentioned are the methoxymethyl, the methoxyethyl and the isopropoxyethyl radicals.

Phenyl-1–4C-alkyl represents one of the abovementioned, phenyl-substituted 1–4C-alkyl radicals. Examples which may be mentioned are the phenethyl and the benzyl radicals.

1–4C-Alkylcarbonyl represents a radical which, in addition to the carbonyl group, contains one of the abovementioned 1–4C-alkyl radicals. An example which may be mentioned is the acetyl radical.

3–7C-Cycloalkylcarbonyl represents a radical which, in addition to the carbonyl group, contains one of the abovementioned 3–7C-cycloalkyl radicals. An example which may be mentioned is the cyclopentylcarbonyl radical.

3–7C-Cycloalkylmethylcarbonyl represents a radical which, in addition to the carbonyl group, contains one of the abovementioned 3–7C-cycloalkylmethyl radicals. An example which may be mentioned is the cyclopropylmethylcarbonyl radical.

1–4C-Alkoxycarbonyl represents a carbonyl group to which one of the abovementioned 1–4C-alkoxy radicals is bonded. Examples which may be mentioned are the methoxycarbonyl [CH$_3$O—C(O)—] and the ethoxycarbonyl [CH$_3$CH$_2$O—C(O)—] radicals.

1–4C-Alkylcarbonyloxy represents a carbonyloxy group to which one of the abovementioned 1–4C-alkyl radicals is bonded. An example which may be mentioned is the acetoxy radical [CH$_3$C(O)—O—].

In addition to the carbonyl group, mono- or di-1–4C-alkylaminocarbonyl radicals contain one of the abovementioned mono- or di-1–4C-alkylamino radicals. Examples which may be mentioned are the N-methyl-, the N,N-dimethyl-, the N-ethyl-, the N-propyl-, the N,N-diethyl- and the N-isopropylamino-carbonyl radicals.

In addition to the nitrogen atom, mono- or di-1–4C-alkylamino radicals contain one or two of the abovementioned 1–4C-alkyl radicals. Di-1–4C-alkylamino is preferred and here, in particular, dimethyl-, di-ethyl- or diisopropylamino.

As a 1–4C-alkylcarbonylamino radical, for example, the propionylamino [C$_3$H$_7$C(O)NH—] and the acetylamino [CH$_3$C(O)NH—] radicals may be mentioned.

Exemplary phenyl radicals substituted by R6, R13 and R20 which may be mentioned are 3-phenoxyphenyl, 4-phenoxyphenyl, 3-benzyloxyphenyl, 4-benzyloxyphenyl, 3-phenethoxyphenyl, 4-phenethoxyphenyl, 3-benzyloxy-4-methoxyphenyl, 4-benzyloxy-3-methoxyphenyl, 3-benzyloxy-5-methoxyphenyl, 4-benzyloxy-3-cyclopropylmethoxyphenyl, 3-cyclopentyloxyphenyl, 4-cyclopentyloxyphenyl, 4-cyclohexyloxyphenyl, 3-cyclohexyloxyphenyl, 3-cyclopropylmethoxyphenyl, 4-cyclopropylmethoxyphenyl, 3-cyclopropylmethoxy-4-methoxyphenyl, 3-cyclopropylmethoxy-4-difluoromethoxyphenyl, 3-cyclopropylmethoxy-4-ethoxyphenyl, 4-cyclopropylmethoxy-3-methoxyphenyl, 3-cyclopropylmethoxy-5-methoxyphenyl, bis-3,4-cyclopropylmethoxyphenyl, bis-3,5-cyclopropylmethoxyphenyl, 3,4-dicyclopentyloxyphenyl, 3-cyclopentyloxy-4-methoxyphenyl, 4-cyclopentyloxy-3-methoxyphenyl, 3-cyclopropylmethoxy-4-cyclopentyloxyphenyl, 3-cyclopentyloxy-5-methoxyphenyl, 4-cyclopropylmethoxy-3-cyclopentyloxyphenyl, 3-cyclobutyloxy-4-methoxyphenyl, 4-(3-hydroxyphenoxy) phenyl, 4-(4-hydroxyphenoxy)phenyl, 3-methoxyethoxy-4-methoxyphenyl, 3-cyclopropylmethoxy-4-acetylaminophenyl, 4-mercaptophenyl, 4-ethylthiophenyl, 2-methylthiophenyl, 4-methylthiophenyl, 4-trifluoromethylthiophenyl, 4-methylthio-3-nitrophenyl, 4-phenylthiophenyl, 3-phenylthiophenyl, 2-methoxy-4-methylthiophenyl, 4-[(4-chlorophenyl)thio]-3-nitrophenyl, 3-methylsulfonyloxyphenyl, 4-methylsulfonyloxyphenyl, 3-(p-toluenesulfonyloxy)phenyl, 4-(p-toluenesulfonyloxy) phenyl, 4-[(4-fluorophenyl)sulfonyloxy]phenyl, 3-[(4-fluorophenyl)sulfonyloxy]-4-nitrophenyl, 3-[(4-chlorophenyl)sulfonyloxy]-4-nitrophenyl, 4-[(4-chlorophenyl)sulfonyloxy]phenyl, 4-[(4-bromophenyl) sulfonyloxy]phenyl, 4-(pyrid-4-ylcarbonyl)phenyl, 4-(4-carboxybenzoyl)phenyl, 4-(2-carboxybenzoyl)phenyl, 4-(2-bromobenzoyl)phenyl, 4-(3-bromobenzoyl)phenyl, 4-(3-methoxybenzoyl)phenyl, 4-(4-methoxybenzoyl)phenyl, 2-benzoylphenyl, 3-benzoylphenyl, 4-benzoylphenyl, 4-(4-chlorobenzoyl)phenyl, 4-(3-chlorobenzoyl)phenyl, 4-(4-cyanobenzoyl)phenyl, 4-(4-nitrobenzoyl)phenyl, 4-(4-methylbenzoyl)phenyl, 3-acetylphenyl, 4-acetylphenyl, 4-ethylcarbonylphenyl, 4-isobutylcarbonylphenyl, 4-cyclopropylmethylcarbonylphenyl, 3,4-diacetylphenyl, 3,5diacetylphenyl, 5acetyl-2-hydroxyphenyl, 3-(piperidin-1-ylcarbonyl)-phenyl, 4-(piperidin-1-yl-carbonyl)phenyl, 4-methoxycarbonylmethylphenyl, 4-(morpholin-4-ylmethyl)phenyl, 4-(4-methylpiperazin-1-ylmethyl)phenyl; 3-dimethylsulfamoyloxyphenyl, 4-dimethylsulfamoyloxyphenyl, 3-chloro-4-dimethylsulfamoyloxyphenyl, 3-methylsulfonyloxy-4- nitrophenyl, 4-chloromethylphenyl, 3-chloromethylphenyl, 3-(phenylsulfonyl)phenyl, 4-(phenylsulfonyl)phenyl, 3-(4-methoxyphenoxy)phenyl, 3-(pyrid-4-yloxy)phenyl, 4-(pyrid-4-yl-oxy)phenyl, 3-pyrrolidinyl-4-methoxyphenyl, 3-(pyrrolidin-2-on-1-yl)phenyl and 3-(pyrrolidin-2,5-dion-1-yl)phenyl.

Possible salts for compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, it being possible to employ the acids in salt preparation—depending on whether a mono- or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can initially be obtained, for example, as process products in the preparation of the compounds according to the invention on an industrial scale are converted into pharmacologically tolerable salts by processes known to the person skilled in the art.

It is known to the person skilled in the art that the compounds according to the invention and their salts, when they are isolated, for example, in crystalline form, can contain various amounts of solvents. The invention therefore also comprises all solvates and in particular all hydrates of the compounds of the formula I, and also all solvates and in particular all hydrates of the salts of the compounds of the formula I.

One embodiment (embodiment a) of the invention are compounds of the formula I, in which R1 is 1–2C-alkoxy, 3–5C-cycloalkoxy, 3–5C-cycloalkylmethoxy or completely or predominantly fluorine-substituted 1–2C-alkoxy, R2 is 1–2-C-alkoxy, 3–5C-cycloalkoxy, 3–5C-cycloalkylmethoxy or completely or predominantly fluorine-substituted 1–2C-alkoxy, R3 is hydrogen, R31 is hydrogen, R4 is hydrogen or 1–2C-alkyl, R5 is hydrogen, R51 is hydrogen, or in which R5 and R51 together represent an additional bond, R6 is O—R7, S—R8, C(O)—R9, CH$_2$—R10, SO$_2$-aryl, O—S(O)$_2$—R11, pyrrolidin-1-yl, pyrrolidin-1-yl-2-one, or pyrrolidin-1-yl-2,5-dione, where R7 is 3–7C-cycloalkyl, 3–7C-cycloalkylmethyl, 1–4C-alkoxy-1–4C-alkyl, aryl or phenyl-1–4C-alkyl, R8 is hydrogen, 1–4C-alkyl, acetyl, phenylcarbonyl, trifluoromethyl or phenyl, R9 is 1–4C-alkyl, 3–7C-cycloalkyl, 3–7C-cycloalkylmethyl, 1-piperidinyl, 1-piperazinyl, 4-methylpiperazinyl, 4-morpholinyl or aryl, R10 is halogen, carboxyl, 1–4C-alkoxy, phenoxy, 1–4C-alkoxycarbonyl, aminocarbonyl, mono- or di-1–4C-alkylaminocarbonyl, N(R15)R16 or 1–4C-alkylcarbonylamino, and R11 is 1–4C-alkyl, mono- or di-1–4C-alkylamino or aryl, aryl is phenyl, pyridyl or R12-substituted phenyl, where R12 is halogen, carboxyl, nitro, amino, cyano, 1–4C-alkyl, trifluoromethyl or 1–4C-alkoxy, R13 is hydrogen, hydroxyl, halogen, cyano, nitro, amino, 1–4C-alkyl, trifluoromethyl, 1–4C-alkoxy, completely or predominantly fluorine-substituted 1–4C-alkoxy, phenyl, phenyl-1–4C-alkyl, C(O)—OR14, C(O)—N(R15)R16, N(R17)R18, S(O)$_2$—R19, S(O)$_2$—N(R15)R16 or has one of the meanings of R6, where R14 is hydrogen or 1–4C-alkyl, R15 is hydrogen or 1–4C-alkyl, R16 is hydrogen, 1–4C-alkyl or aryl, or where R15 and R16, together and including the nitrogen atom to which both are bonded, are a 1-piperidyl, 1-piperazinyl, 1-methylpiperazin-4-yl or 4-morpholinyl radical, R17 is hydrogen, 1–4C-alkyl, S(O)$_2$—R19 or S(O)$_2$-aryl, R18 is 1–4C-alkyl, 1–4C-alkylcarbonyl, 3–7C-cycloalkylcarbonyl, 3–7C-cycloalkylmethylcarbonyl, S(O)$_2$—R19 or S(O)$_2$-aryl, and R19 is 1–4C-alkyl, R20 is hydrogen, hydroxyl, halogen, nitro, amino, 1–4C-alkyl, trifluoromethyl, 1–4C-alkoxy, completely or predominantly fluorine-substituted 1–4C-alkoxy, 3–7C-cycloalkoxy, 3–7C-cycloalkyl-methoxy, carboxyl, 1–4C-alkoxycarbonyl or 1–4C-alkylcarbonyloxy, and the salts, the N-oxides and the salts of the N-oxides of these compounds.

Compounds of the formula I of embodiment a to be emphasized are those in which

R1 is 1–2C-alkoxy,

R2 is 1–2C-alkoxy,

R3, R31, R4, R5 and R51 are hydrogen,

R6 is O—R7, S—R8, C(O)—R9, CH$_2$—R10, S(O)$_2$-phenyl, O—S(O)$_2$—R11, pyrrolidin-1-yl, pyrrolidin-1-yl-2-one or pyrrolidin-1-yl-2,5-dione, where R7 is 3–5C-cycloalkyl, 3–5C-cycloalkylmethyl, 1–2C-alkoxy-1–2C-alkyl, aryl or phenyl-1–2C-alkyl, R8 is phenyl, R9 is 1–4C-alkyl, 3–5C-cycloalkylmethyl, 1-piperidinyl or aryl, R10 is halogen, 1–4C-alkoxycarbonyl or N(R15)R16, and R11 is methyl or 4-methylphenyl, aryl is phenyl, pyridyl or R12-substituted phenyl, where R12 is 1–4C-alkyl, 1–4C-alkoxy, halogen, nitro or cyano, R15 is 1–4C-alkyl, and R16 is 1–4C-alkyl, or where R15 and R16, together and including the nitrogen atom to which both are bonded, are a 1-piperidinyl, 1-piperazinyl, 1-methylpiperazin-4-yl or 4-morpholinyl radical, and in which either R13 is hydrogen, 1–4C-alkoxy, completely or predominantly fluorine-substituted 1–2C-alkoxy, or 1–4C-alkylcarbonylamino and R20 is hydrogen, or R13 is hydrogen and R20 is 3–5C-cycloalkoxy or 3–5C-cycloalkylmethoxy, and the salts, the N-oxides and the salts of the N-oxides of these compounds.

Compounds of the formula I of embodiment a particularly to be emphasized are those in which R1 is 1–2C-alkoxy, R2 is 1–2C-alkoxy, R3, R31, R4, R5 and R51 are hydrogen, R6 is O—R7, S—R8, C(O)—R9, CH$_2$—R10, S(O)$_2$-phenyl, O—S(O)$_2$—R11, pyrrolidin-1-yl or pyrrolidin-1-yl-2-one, where R7 is cyclobutyl, cyclopentyl, cyclopropylmethyl, 2-methoxyethyl, phenyl, 4-methoxyphenyl, benzyl, phenethyl or pyridyl, R8 is phenyl, R9 is methyl, ethyl, isobutyl, cyclopropylmethyl, 1-piperidinyl or aryl, R10 is methoxycarbonyl, morpholin-4-yl or 1-methylpiperazin-4-yl, and R11 is methyl or 4-methylphenyl, aryl is phenyl, pyridyl or R12-substituted phenyl, in which R12 is methoxy, halogen, nitro or cyano, and in which either R13 is hydrogen, methoxy, ethoxy, difluoromethoxy or acetylamino and R20 is hydrogen, or R13 is hydrogen and R20 is cyclopropylmethoxy, and the salts, the N-oxides and the salts of the N-oxides of these compounds.

Another embodiment (embodiment b) of the invention are compounds of the formula I in which R1 is hydroxyl, 1–4C-alkoxy, 3–7C-cycloalkoxy, 3–7C-cycloalkylmethoxy or completely or predominantly fluorine-substituted 1–4C-alkoxy, R2 is hydroxyl, 1–4C-alkoxy, 3–7C-cycloalkoxy, 3–7C-cycloalkylmethoxy or completely or predominantly fluorine-substituted 1–4C-alkoxy, or in which R1 and R2 together are a 1–2C-alkylenedioxy group, R3 is hydrogen or 1–4C-alkyl, R31 is hydrogen or 1–4C-alkyl, or in which R3 and R31 together are a 1–4C-alkylene group, R4 is hydrogen or 1–4C-alkyl, R5 is hydrogen, R51 is hydrogen, or in which R5 and R51 together are an additional bond, R6 is O—R7, S—R8, C(O)—R9, CH$_2$—R10 or O—S(O)$_2$—R11, where R7 is 3–7C-cycloalkyl, 3–7C-cycloalkylmethyl, aryl or phenyl-1–4C-alkyl, R8 is hydrogen, 1–4C-alkyl, 1–4C-alkylcarbonyl, trifluoromethyl, difluoromethyl, trichloromethyl or phenyl, R9 is 1–4C-alkyl, 1-pyrrolidinyl, 1-piperidinyl, 1-piperazinyl, 4-methylpiperazinyl, 4-morpholinyl or aryl, R10 is hydroxyl, halogen, cyano, carboxyl, 1–4C-alkoxy, phenoxy, 1–4C-alkoxycarbonyl, aminocarbonyl, mono- or di-1–4C-alkylaminocarbonyl, N(R15)R16 or 1–4C-alkylcarbonylamino, and R11 is 1–4C-alkyl, amino, mono- or di-1–4C-alkylamino or aryl, aryl is phenyl, pyridyl or R12-substituted phenyl, where R12 is hydroxyl, halogen, carboxyl, nitro, amino, cyano, 1–4C-alkyl, trifluoromethyl, 1–4C-alkoxy, 1–4C-alkoxycarbonyl, 1–4C-alkylcarbonylamino, 1–4C-alkylcarbonyloxy or aminocarbonyl, R13 is hydrogen, hydroxyl, halogen, cyano, nitro, amino, 1–4C-alkyl, trifluoromethyl, 1–4C-alkoxy, completely or predominantly fluorine-substituted 1–4C-alkoxy, phenyl, phenyl-1–4C-alkyl, C(O)—OR14, C(O)—N(R15)R16, N(R17)R18, S(O)$_2$—R19, S(O)$_2$—N(R15)R16 or has one of the meanings of R6, where R14 is hydrogen, 1–4C-alkyl, 3–7C-cycloalkyl or 3–7C-cycloalkylmethyl, R15 is hydrogen, 1–4C-alkyl, 3–7C-cycloalkyl or 3–7C-cycloalkylmethyl, R16 is hydrogen, 1–4C-alkyl, 3–7C-cycloalkyl, 3–7C-cycloalkylmethyl or aryl, or where R15 and R16, together and including the nitrogen atom to which both are bonded, are a 1-pyrrolidinyl, 1-piperidinyl, 1-piperazinyl, 4-methylpiperazin-1-yl, 1-hexahydroazepinyl or 4-morpholinyl radical, R17 is hydrogen, 1–4C-alkyl, S(O)$_2$—R19 or S(O)$_2$-aryl, R18 is 1–4C-alkyl, 1–4C-alkylcarbonyl or S(O)$_2$—R19 or S(O)$_2$-aryl, and R19 is 1–4C-alkyl, R20 is hydrogen, hydroxyl, halogen, nitro, amino, 1–4C-alkyl, trifluoromethyl, 1–4C-alkoxy, completely or predominantly fluorine-substituted 1–4C-alkoxy, 3–7C-cycloalkoxy, 3–7C-cycloalkylmethoxy, CH$_2$—R10, carboxyl, 1–4C-alkoxycarbonyl, 1–4C-alkylcarbonyloxy, 1–4C-alkylcarbonylamino or aminocarbonyl, and the salts, the N-oxides and the salts of the N-oxides of these compounds.

Compounds of the formula I of embodiment b to be emphasized are those in which

R1 is 1–2C-alkoxy, 3–5C-cycloalkoxy, 3–5C-cycloalkylmethoxy or completely or predominantly fluorine-substituted 1–2C-alkoxy, R2 is 1–2C-alkoxy, 3–5C-cycloalkoxy, 3–5C-cycloalkylmethoxy or completely or predominantly fluorine-substituted 1–2C-alkoxy, R3 is hydrogen, R31 is hydrogen, R4 is hydrogen or 1–2C-alkyl, R5 is hydrogen, R51 is hydrogen, or in which R5 and R51 together represent an additional bond, R6 is O—R7, S—R8, C(O)—R9, CH$_2$—R10 or O—S(O)$_2$—R11, where R7 is 3–7C-cycloalkyl, 3–7C-cycloalkylmethyl, aryl or phenyl-1–4C-alkyl, R8 is hydrogen, 1–4C-alkyl, acetyl, trifluoromethyl or phenyl, R9 is 1–4C-alkyl, 1-piperidinyl, 1-piperazinyl, 4-methylpiperazinyl, 4-morpholinyl or aryl, R10 is halogen, carboxyl, 1–4C-alkoxy, phenoxy, 1–4C-alkoxycarbonyl, aminocarbonyl, mono- or di-1–4C-alkylaminocarbonyl, N(R15)R16 or 1–4C-alkylcarbonylamino, and R11 is 1–4C-alkyl, mono- or di-1–4C-alkylamino or aryl, aryl is phenyl, pyridyl or R12-substituted phenyl, where R12 is halogen, carboxyl, nitro, amino, cyano, 1–4C-alkyl, trifluoromethyl or 1–4C-alkoxy, R13 is hydrogen, hydroxyl, halogen, cyano, nitro, amino, 1–4C-alkyl, trifluoromethyl, 1–4C-alkoxy, completely or predominantly fluorine-substituted 1–4C-alkoxy, phenyl, phenyl-1–4C-alkyl, C(O)—OR14, C(O)—N(R15)R16, N(R17)R18, S(O)$_2$—R19, S(O)$_2$—N(R15)R16 or has one of the meanings of R6, where R14 is hydrogen or 1–4C-alkyl, R15 is hydrogen or 1–4C-alkyl, R16 is hydrogen, 1–4C-alkyl or aryl, or where R15 and R16, together and including the nitrogen atom to which both are bonded, are a 1-piperidyl, 1-piperazinyl, 4-methylpiperazin-1-yl or 4-morpholinyl radical, R17 is hydrogen, 1–4C-alkyl, S(O)$_2$—R19 or S(O)$_2$-aryl, R18 is 1–4C-alkyl, 1–4C-alkylcarbonyl, S(O)$_2$—R19 or S(O)$_2$-aryl, and R19 is 1–4C-alkyl, R20 is hydrogen, hydroxyl, halogen, nitro, amino, 1–4C-alkyl, trifluoromethyl, 1–4C-alkoxy, completely or predominantly fluorine-substituted 1–4C-alkoxy, 3–7C-cycloalkoxy, 3–7C-cycloalkylmethoxy, carboxyl, 1–4C-alkoxycarbonyl or 1–4C-alkylcarbonyloxy, and the salts, the N-oxides and the salts of the N-oxides of these compounds.

Compounds of the formula I of embodiment b particularly to be emphasized are those in which R1 is 1–2C-alkoxy, R2 is 1–2C-alkoxy, R3, R31, R4, R5 and R51 are hydrogen, R6 is O—R7, S—R8, C(O)—R9, CH$_2$—R10 or O—S(O)$_2$—R11, where R7 is 3–5C-cycloalkyl, 3–5C-cycloalkylmethyl, phenyl or phenyl-1–2C-alkyl, R8 is phenyl, R9 is methyl, 1-piperidinyl or phenyl, R10 is halogen, 1–4C-alkoxycarbonyl or N(R15)R16 and R11 is methyl or 4-methylphenyl, R15 is 1–4C-alkyl and R16 is 1–4C-alkyl, or where R15 and R16, together and including the nitrogen atom to which both are bonded, are a 1-piperidinyl, 1-piperazinyl, 1-methylpiperazin-4-yl or 4-morpholinyl radical, and in which either R13 is hydrogen, methoxy or ethoxy and R20 is hydrogen, or R13 is hydrogen and R20 is 3–5C-cycloalkoxy or 3–5C-cycloalkylmethoxy, and the salts, the N-oxides and the salts of the N-oxides of these compounds.

Preferred compounds of the formula I of embodiment b are those in which

R1 is 1–2C-alkoxy,

R2 is 1–2C-alkoxy,

R3, R31, R4, R5 and R51 are hydrogen,

R6 is O—R7, S—R8, C(O)—R9, CH$_2$—R10 or O—S(O)$_2$—R11, where

R7 is cyclopentyl, cyclopropylmethyl, phenyl, benzyl or phenethyl,

R8 is phenyl,

R9 is methyl, 1-piperidinyl or phenyl,

R10 is halogen, methoxycarbonyl, morpholin-4-yl or 1-methylpiperazin-4-yl and

R11 is methyl or 4-methylphenyl, and in which either

R13 is hydrogen or methoxy and

R20 is hydrogen, or

R13 is hydrogen and

R20 is cyclopropylmethoxy and the salts, the N-oxides and the salts of the N-oxides of these compounds.

A further embodiment (embodiment c) of the invention are compounds of the formula I in which R1 is 1–2C-alkoxy, 3–5C-cycloalkoxy, 3–5C-cycloalkylmethoxy or completely or predominantly fluorine-substituted 1–2C-alkoxy, R2 is 1–2C-alkoxy, 3–5C-cycloalkoxy, 3–5C-cycloalkylmethoxy or completely or predominantly fluorine-substituted 1–2C-alkoxy, R3 is hydrogen, R31 is hydrogen, R4 is hydrogen or 1–2C-alkyl, R5 is hydrogen, R51 is hydrogen, or where R5 and R51 together represent an additional bond, R6 is O—R7, S—R8, C(O)—R9, CH$_2$—R10, S(O)$_2$-phenyl or O—S(O)$_2$—R11, where R7 is 3–5C-cycloalkyl, 3–5C-cycloalkylmethyl, 1–2C-alkoxy-1–2C-alkyl, aryl or phenyl-1–2C-alkyl, R8 is phenyl, R9 is 1–4C-alkyl, 3–5C-cycloalkylmethyl, 1-piperidinyl or aryl, R10 is halogen and R11 is 1–4C-alkyl or aryl, aryl is phenyl or R12-substituted phenyl, where R12 is halogen, nitro, 1–4C-alkyl or 1–4C-alkoxy, R13 is hydrogen, 1–4C-alkoxy, 1–4C-alkylcarbonylamino or completely or predominantly fluorine-substituted 1–2C-alkoxy, and R20 is hydrogen, 3–5C-cycloalkoxy or 3–5C-cycloalkylmethoxy, and the salts, the N-oxides and the salts of the N-oxides of these compounds.

Compounds of the formula I of embodiment c to be emphasized are those in which

R1 is 1–2C-alkoxy,

R2 is 1–2C-alkoxy,

R3, R31, R4, R5 and R51 are hydrogen,

R6 is O—R7, S—R8, C(O)—R9, CH$_2$—R10, S(O)$_2$-phenyl or O—S(O)$_2$—R11, where

R7 is 3–5C-cycloalkyl, 3–5C-cycloalkylmethyl, 1–2C-alkoxy-1–2C-alkyl, aryl or phenyl-1–2C-alkyl, R8 is phenyl, R9 is 1–4C-alkyl, 3–5C-cycloalkylmethyl, 1-piperidinyl or aryl, R10 is halogen, R11 is 1–4C-alkyl or aryl, aryl is phenyl or R12-substituted phenyl, where R12 is halogen, nitro, 1–4C-alkyl or 1–4C-alkoxy, R13 is hydrogen, 1–4C-alkoxy, 1–4C-alkylcarbonylamino or completely or predominantly fluorine-substituted 1–2C-alkoxy, and R20 is hydrogen, 3–5C-cycloalkoxy or 3–5C-cycloalkylmethoxy, and the salts, the N-oxides and the salts of the N-oxides of these compounds.

Preferred compounds of the formula I of embodiment c are those in which

R1 is 1–2C-alkoxy,

R2 is 1–2C-alkoxy,

R3, R31, R4, R5 and R51 are hydrogen,

R6 is acetyl, ethylcarbonyl, isobutylcarbonyl, cyclopropylmethylcarbonyl, benzoyl, 4-methoxyphenylcarbonyl, 4-chlorophenylcarbonyl, 3-chloro-phenylcarbonyl, 4-nitrophenylcarbonyl, thiophenoxy, phenoxy, 4-methoxyphenyloxy, benzyloxy, phenethyloxy, methylsulfonyloxy, 4-methylphenylsulfonyloxy, phenylsulfonyl, 4-chloromethyl or piperid-1-ylcarbonyl, R13 is hydrogen and R20 is hydrogen, and the salts, the N-oxides and the salts of the N-oxides of these compounds.

Further preferred compounds of the formula I of embodiment c are those in which

R1 is 1–2C-alkoxy,

R2 is 1–2C-alkoxy,

R3, R31, R4, R5 and R51 are hydrogen,

R6 is benzyloxy, methoxyethoxy, cyclopropylmethoxy or cyclobutoxy, and in which either R13 is methoxy, ethoxy or acetylamino and R20 is hydrogen, or R13 is hydrogen and R20 is cyclopropylmethoxy, and the salts, the N-oxides and the salts of the N-oxides of these compounds.

Particularly preferred compounds of the formula I of embodiment c are those in which R1 is methoxy, R2 is methoxy or ethoxy, R3, R31, R4, R5 and R51 are hydrogen, R6 is acetyl, benzoyl, phenoxy or piperid-1-ylcarbonyl, R13 is hydrogen and R20 is hydrogen, and the salts, the N-oxides and the salts of the N-oxides of these compounds.

Further particularly preferred compounds of the formula I of embodiment c are those in which R1 is methoxy, R2 is methoxy or ethoxy, R3, R31, R4, R5 and R51 are hydrogen, R6 is cyclopropylmethoxy or cyclobutoxy, and in which either R13 is methoxy or ethoxy and R20 is hydrogen, or R13 is hydrogen and R20 is cyclopropylmethoxy, and the salts, the N-oxides and the salts of the N-oxides of these compounds.

The compounds of the formula I are chiral compounds having chiral centers in positions 4a and 10b and, depending on the meaning of the substituents R3, R31, R4, R5 and R51, further chiral centers in the positions 1, 2, 3 and 4. Numbering

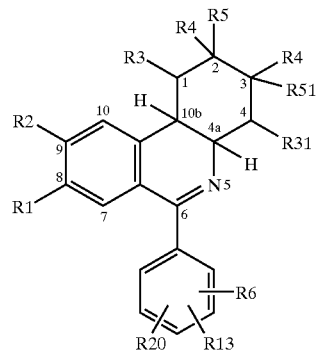

(I)

The invention therefore comprises all conceivable pure diastereomers and pure enantiomers and their mixtures in any mixing ratio, including the racemates. The compounds of the formula I are preferred in which the hydrogen atoms in positions 4a and 10b are cis to one another. The pure cis enantiomers are particularly preferred.

In this connection, particularly preferred compounds of the formula I are those in which positions 4a and 10b have the same absolute configuration as the compound (−)-cis-1,2-dimethoxy-4-(2-aminocyclohexyl)benzene employable as a starting compound and having the optical rotation $[\alpha]_D^{20}=-58.5°$ (c=1, ethanol).

The enantiomers can be separated in a manner known per se (for example by preparation and separation of appropriate diastereoisomeric compounds). Preferably, an enantiomer separation is carried out at the stage of the starting compounds of the formula IV

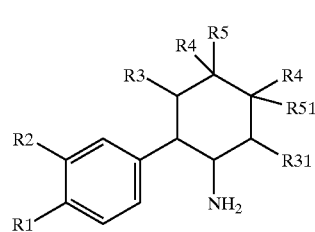

(IV)

for example by means of salt formation of the racemic compounds of the formula IV with optically active carboxylic acids. Examples which may be mentioned in this connection are the enantiomeric forms of mandelic acid, tartaric acid, O,O'-dibenzoyltartaric acid, camphoric acid, quinic acid, glutamic acid, malic acid, camphorsulfonic acid, 3-bromocamphorsulfonic acid, α-methoxyphenylacetic acid, α-methoxy-α-trifluoromethylphenylacetic acid and 2-phenylpropionic acid. Alternatively, enantiomerically pure starting compounds of the formula IV can also be prepared via asymmetric syntheses.

The preparation of the compounds of the formula I in which R1, R2, R3, R31, R4, R5, R51, R6, R13 and R20 have the meanings indicated above and their salts can be carried out, for example, by the process described below in greater detail.

The process comprises cyclocondensing compounds of the formula II

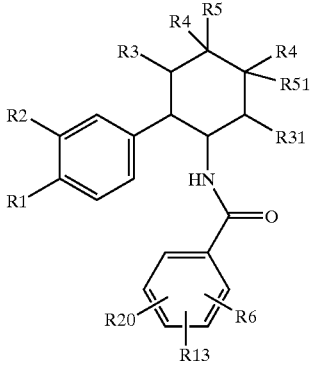

(II)

in which R1, R2, R3, R31, R4, R5, R51, R6, R13 and R20 have the meanings indicated above, and, optionally, then converting the compounds of the formula I obtained into their salts, or, optionally, then converting salts of the compounds of the formula I obtained into the free compounds.

Compounds of the formula I obtained can be converted, optionally, into further compounds of the formula I by derivatization.

For example, from compounds of the formula I in which a) R12 and/or R13 and/or R20 are an ester group, the corresponding acids can be obtained by acidic or alkaline hydrolysis, or the corresponding amides can be prepared by reaction with suitably substituted amines;

b) R12 and/or R20 are a 1–4C-alkylcarbonyloxy group, the corresponding hydroxyl compounds can be obtained by acidic or alkaline hydrolysis;

c) one or more of the radicals R10, R12, R13 and R20 are a nitro group, the corresponding amino compounds, which, for their part, can again be further derivatized, can be obtained by selective catalytic hydrogenation.

The methods mentioned under a), b) and c) are expediently carried out analogously to the methods known to the person skilled in the art.

In addition, the compounds of the formula I can be converted, optionally, into their N-oxides, for example with the aid of hydrogen peroxide in methanol or with the aid of m-chloroperoxybenzoic acid in di-chloromethane. The person skilled in the art is familiar on the basis of his/her expert knowledge with the reaction conditions which are specifically necessary for carrying out the N-oxidation.

The cyclocondensation is carried out in a manner known per se to the person skilled in the art, according to Bischler-Napieralski (e.g. as described in J. Chem. Soc., 1956, 4280–4282) in the presence of a suitable condensing agent, such as, for example, polyphosphoric acid, phosphorus pentachloride, phosphorus pentoxide or preferably phosphorus oxychloride, in a suitable inert solvent, e.g. in a chlorinated hydrocarbon such as chloroform, or in a cyclic hydrocarbon such as toluene or xylene, or another inert solvent such as acetonitrile, or without further solvent using an excess of condensing agent, preferably at elevated temperature, in particular at the boiling temperature of the solvent or condensing agent used.

Compounds of the formula II in which R1, R2, R3, R31, R4, R5, R51, R6, R13 and R20 have the meanings indicated above are accessible from the corresponding compounds of the formula IV, in which R1, R2, R3, R31, R4, R5 and R51 have the meanings indicated above, by reaction with compounds of the formula III,

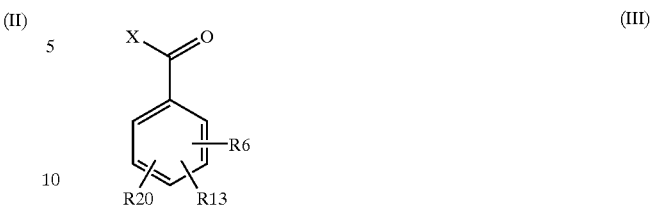

(III)

in which R6, R13 and R20 have the meanings indicated above and X represents a suitable leaving group, preferably a chlorine atom. For example, the acylation or benzoylation is carried out as described in the following examples or as in J. Chem. Soc. (C), 1971, 1805–1808.

Compounds of the formula III and compounds of the formula IV are either known or can be prepared in a known manner.

The compounds of the formula IV can be prepared, for example, from compounds of the formula V,

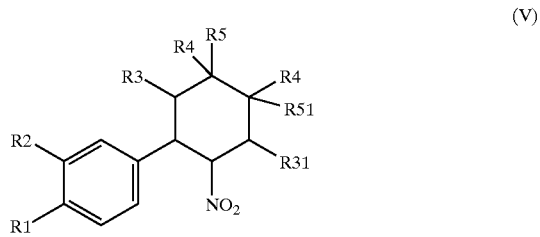

(V)

in which R1, R2, R3, R31, R4, R5 and R51 have the abovementioned meanings, by reduction of the nitro group.

The reduction is carried out in a manner known to the person skilled in the art, for example as described in J. Org. Chem. 1962, 27, 4426 or as described in the following examples.

The reduction can be carried out, for example, by catalytic hydrogenation, e.g. in the presence of Raney nickel, in a lower alcohol such as methanol or ethanol at room temperature and under normal or elevated pressure. Optionally, a catalytic amount of an acid, such as, for example, hydrochloric acid, can be added to the solvent. Preferably, however, the reduction is carried out using metals such as zinc or iron with organic acids such as acetic acid or mineral acids such as hydrochloric acid.

The compounds of the formula IV in which R1, R2, R3, R31 and R4 have the meanings indicated above and R5 and R51 together represent an additional bond can be prepared from the corresponding compounds of the formula V by selective reduction of the nitro group in a manner known to the person skilled in the art, for example in the presence of Raney nickel in a lower alcohol as solvent using hydrazine hydrate as a hydrogen donor.

The compounds of the formula V, in which R1, R2, R3, R31 and R4 have the meanings indicated above and R5 and R51 are hydrogen, are either known or can be prepared from corresponding compounds of the formula V in which R5 and R51 together are an additional bond. The reaction can be carried out in a manner known to the person skilled in the art, preferably by hydrogenation in the presence of a catalyst, such as, for example, palladium on active carbon, e.g. as described in J. Chem. Soc. (C), 1971, 1805–1808.

The compounds of the formula V, in which R5 and R51 together are an additional bond, are either known or can be obtained by the reaction of compounds of the formula VI,

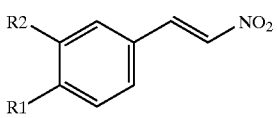

in which R1 and R2 have the meanings mentioned above, with compounds of the formula VII,

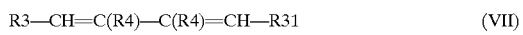

in which R3, R31 and R4 have the meanings mentioned above.

Compounds of the formula V in which R5 and R51 together are an additional bond and R3 and R31 together are a 1–4C-alkylene group can be obtained, for example, by reaction of cyclic compounds of the formula VII, in which R4 has the meanings indicated above and R3 and R31 together are a 1–4C-alkylene group [e.g. cyclohexa-1,3-diene, 2,3-dimethylcyclohexa-1,3-diene, cyclohepta-1,3-diene, 2,3-dimethylcyclohepta-1,3-diene or cycloocta-1,3-diene] with compounds of the formula VI in which R1 and R2 have the abovementioned meanings.

The cycloaddition is in this case carried out in a manner known to the person skilled in the art according to Diels-Alder, e.g. as described in J. Amer. Chem. Soc. 1957, 79, 6559 or in J. Org. Chem. 1952, 17, 581 or as described in the following examples.

Compounds of the formula V obtained in the cycloaddition, in which the phenyl ring and the nitro group are trans to one another, can be converted in a manner known to the person skilled in the art into the corresponding cis compounds, e.g. as described in J. Amer. Chem. Soc. 1957, 79, 6559 or as described in the following examples.

The compounds of the formulae VI and VII are either known or can be prepared in a known manner. The compounds of the formula VI can be prepared, for example, in a manner known to the person skilled in the art from corresponding compounds of the formula VIII as described, for example, in J. Chem. Soc. 1951, 2524 or in J. Org. Chem. 1944, 9, 170 or as described in the following examples.

The compounds of the formula VIII,

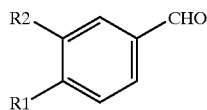

in which R1 and R2 have the meanings indicated above, are either known or can be prepared in a manner known to the person skilled in the art, as described, for example, in Ber. Dtsch. Chem. Ges. 1925, 58, 203.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1991.

The isolation and purification of the substances according to the invention is carried out in a manner known per se, e.g. by distilling off the solvent in vacuo and recrystallizing the resulting residue from a suitable solvent or subjecting it to one of the customary purification methods, such as, for example, column chromatography on suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low molecular weight aliphatic alcohol such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically intolerable salts can be converted into pharmacologically tolerable salts.

The following examples serve to illustrate the invention further without restricting it. Likewise, further compounds of the formula I, whose preparation is not explicitly described, can be prepared in an analogous manner or in a manner familiar per se to the person skilled in the art using customary process techniques.

In the examples, m.p stands for melting point, h for hour(s), RT for room temperature, EF for empirical formula, MW for molecular weight, calc. for calculated, fnd for found. The compounds mentioned in the examples and their salts are a preferred subject of the invention.

EXAMPLES

Final Products 1. (−)-cis-8,9-Dimethoxy-6-(4-benzoylphenyl)-1,2,3,4,4a,10b-hexahydrophenanthridine 7.1 g of (−)-cis-N-[2-(3,4-Dimethoxyphenyl)cyclohexyl]-4-benzoylbenzamide (compound A1) are dissolved in 100 ml of acetonitrile and 5.0 ml of phosphoryl chloride and stirred overnight at 80° C. The reaction mixture is concentrated under reduced pressure and the residue is extracted with satd sodium hydrogencarbonate solution and ethyl acetate. After chromatography on silica gel using petroleum ether (low)/ethyl acetate/triethylamine in the ratio 6/3/1 and concentration of the product fractions, 5.3 g of the title compound are obtained.

EF: $C_{28}H_{27}NO_3$; MW: 425.53

Elemental analysis×0.08 $H_2O$: calc.: C, 78.77; H, 6.41; N, 3.28. fnd: C, 78.55; H, 6.64; N, 3.50.

Optical rotation: $[\alpha]_D^{20}$=−70.6° (c=0.2, ethanol)

Starting from the starting compounds described below, the following are obtained according to the procedure as in Example 1:

2. (−)-cis-8,9-Dimethoxy-6-(4-acetophenyl)-1,2,3,4,4a,10b-hexahydrophenanthridine

EF: $C_{23}H_{25}NO_3$; MW: 363.46

Elemental analysis: calc.: C, 76.01; H, 6.93; N, 3.85. fnd: C, 75.77; H, 6.98; N, 3.82.

Optical rotation: $[\alpha]_D^{20}$=−97.4° (c=0.2, ethanol)

3. (−)-cis-8,9-Dimethoxy-6-(3-benzoylphenyl)-1,2,3,4,4a,10b-hexahydrophenanthridine

EF: $C_{28}H_{27}NO_3$; MW: 425.53

Elemental analysis×0.15 $H_2O$: calc.: C, 78.54; H, 6.43; N, 3.27. fnd: C, 78.39; H, 6.58; N, 3.40.

4. (−)-cis-8,9-Dimethoxy-6-(4-phenoxyphenyl)-1,2,3,4,4a,10b-hexahydrophenanthridine EF: $C_{27}H_{27}NO_3$; MW: 413.52; m.p. 110–115° C.
Elemental analysis: calc.: C, 78.42; H, 6.58; N, 3.39. fnd: C, 78.44; H, 6.61; N, 3.29.
Optical rotation: $[\alpha]_D^{20}=-63°$ (c=0.2, ethanol)

5. (−)-cis-8,9-Dimethoxy-6-(3-phenoxyphenyl)-1,2,3,4,4a,10b-hexahydrophenanthridine EF: $C_{27}H_{27}NO_3$; MW: 413.52
Elemental analysis×0.23 $H_2O$: calc.: C, 77.64; H, 6.63; N, 3.35. fnd: C, 77.77; H, 6.71; N, 3.22.
Optical rotation: $[\alpha]_D^{20}=-46,4°$ (c=0.2, ethanol)

6. (−)-cis-8,9-Dimethoxy-6-[3-(phenylthio)phenyl]-1,2,3,4,4a,10b-hexahydrophenanthridine EF: $C_{27}H_{27}NO_2S$; MW: 429.59
Elemental analysis×0.32 $H_2O$: calc.: C, 74.48; H, 6.40; N, 3.22; S,7.36. fnd: C, 74.82; H, 6.44; N, 3.22; S,7.02.
Optical rotation: $[\alpha]_D^{20}=-66°$ (c=0.2, ethanol)

7. (−)-cis-8,9-Dimethoxy-6-(3-benzyloxyphenyl)-1,2,3,4,4a,10b-hexahydrophenanthridine EF: $C_{28}H_{29}NO_3$; MW: 427.55; m.p. 118–120° C.
Elemental analysis: calc.: C, 78.66; H, 6.83; N, 3.28. fnd: C, 78.62; H, 6.90; N, 3.26.
Optical rotation: $[\alpha]_D^{20}=-79.2°$ (c=0.2, ethanol)

8. (−)-cis-8,9-Dimethoxy-6-(3-phenethyloxyphenyl)-1,2,3,4,4a,10b-hexahydrophenanthridine EF: $C_{29}H_{31}NO_3$; MW: 441.58
Elemental analysis×0.2 $H_2O$: calc.: C, 78.24; H, 7.11; N, 3.15. fnd: C, 78.29; H, 7.26; N, 3.03
Optical rotation: $[\alpha]_D^{20}=-73.6°$ (c=0.2, ethanol)

9. (−)-cis-6-(3-Cyclopentyloxy-4-methoxyphenyl)-8,9-dimethoxy-1,2,3,4,4a,10b-hexahydrophenanthridine EF: $C_{27}H_{33}NO_4$; MW: 435.57
Elemental analysis×0.2 $H_2O$: calc.: C, 73.84; H, 7.67; N, 3.19. fnd: C, 73.59; H, 7.86; N, 3.48.
Optical rotation: $[\alpha]_D^{20}=-78.5°$ (c=0.2, ethanol)

10. (−)-cis-6-(4-Benzyloxy-3-cyclopropylmethoxyphenyl)-8,9-dimethoxy-1,2,3,4,4a,10b-hexahydrophenanthridine EF: $C_{32}H_{35}NO_4$; MW: 497.64
Elemental analysis×0.27 $H_2O$: calc.: C, 76.50; H, 7.13; N, 2.79. fnd: C, 76.44; H7.12; N2.85.
Optical rotation: $[\alpha]_D^{20}=-72.2°$ (c=0.2, ethanol)

11. (+)-cis-6-(3-Benzyloxy-4-methoxyphenyl)-8,9-dimethoxy-1,2,3,4,4a,10b-hexahydrophenanthridine EF: $C_{29}H_{31}NO_4$; MW: 457.57
Elemental analysis×0.22 $H_2O$: calc.: C, 75.46; H, 6.87; N, 3.03. fnd: C, 75.57; H, 6.96; N, 2.92.
Optical rotation: $[\alpha]_D^{20}=+83.8°$ (c=0.2, ethanol)

12. (−)-cis-8,9-Dimethoxy-6-[3-cyclopropylmethoxy4-methoxyphenyl]-1,2,3,4,4a,10b-hexahydrophenanthridine EF: $C_{26}H_{31}NO_4$; MW: 421.54
Elemental analysis: calc.: C, 74.08; H, 7.41; N, 3.32. fnd: C, 73.84; H, 7.54; N, 3.44.
Optical rotation: $[\alpha]_D^{20}=-92.2°$ (c=0.2, ethanol)

13. (−)-cis-8,9-Dimethoxy-6-(3-methanesulfonyloxyphenyl)-1,2,3,4,4a,10b-hexahydrophenanthridine EF: $C_{22}H_{25}NO_5S$; MW: 415.51
Elemental analysis×0.35 $H_2O$: calc.: C, 62.63; H, 6.14; N, 3.32. fnd: C, 62.97; H, 6.26; N, 3.14.
Optical rotation: $[\alpha]_D^{20}=-82.6°$ (c=0.2, ethanol)

14. (−)-cis-8,9-Dimethoxy-6-[3-(p-toluenesulfonyloxy)phenyl]-1,2,3,4,4a,10b-hexahydrophenanthridine EF: $C_{28}H_{29}NO_5S$; MW: 491.61
Elemental analysis×0.45 $H_2O$: calc.: C, 67.30; H, 6.03; N, 2.80; S, 6.42. fnd: C, 67.52; H, 6.03; N, 2.58; S, 6.20.
Optical rotation: $[\alpha]_D^{20}52.2°$ (c=0.2, ethanol)

15. (−)-cis-8,9-Dimethoxy-6-[3,4-bis-(cyclopropylmethoxy)phenyl]-i,2,3,4,4a,10b-hexahydrophenanthridine EF: $C_{29}H_{35}NO_4$; MW: 461.61
Elemental analysis×0.13 $H_2O$: calc.: C, 75.08; H, 7.66; N, 3.02. fnd: C, 74.90; H, 7.64; N, 3.21.
Optical rotation: $[\alpha]_D^{20}=-80°$ (c=0.2, ethanol)

16. (−)-cis-8,9-Dimethoxy-[4-(piperdin-1-ylcarbonyl)phenyl]-1,2,3,4,4a,10b-hexahydrophenanthridine EF: $C_{27}H_{32}N_2O_3$; MW: 432.57
Elemental analysis: calc.: C, 75.95; H, 7.53; N, 6.09. fnd: C, 75.80; H, 7.55; N, 5.79.
Optical rotation: $[\alpha]_D^{20}=-57.6°$ (c=0.2, ethanol)

17. (−)-cis-8,9-Dimethoxy-[3-(piperidin-1-ylcarbonyl)phenyl]-1,2,3,4,4a,10b-hexahydrophenanthridine EF: $C_{27}H_{32}N_2O_3$; MW: 432.57, m.p. 182–185° C.
Elemental analysis: calc.: C, 75.95; H, 7.53; N, 6.09. fnd: C, 75.19; H, 7.49; N, 6.28.
Optical rotation: $[\alpha]_D^{20}=-83.6°$ (c=0.2, ethanol)

18. (−)-cis-8,9-Dimethoxy-6-(4-methoxycarbonylmethylphenyl)-1,2,3,4,4a,10b-hexahydrophenanthridine EF: $C_{24}H_{27}NO_4$; MW: 393.49; m.p. 124–125° C.
Elemental analysis: calc.: C, 73.26; H, 6.92; N, 3.56. fnd: C, 73.34; H, 6.94; N, 3.55.
Optical rotation: $[\alpha]_D^{20}=-91°$ (c=0.2, ethanol)

19. cis-6-(4-Chloromethylphenyl)-9-ethoxy-8-methoxy-1,2,3,4,4a,10b-hexahydrophenanthridine EF: $C_{23}H_{26}Cl\,NO_2$; MW: 383.92; m.p. 151–153° C.
Elemental analysis×0.25 $H_2O$: calc.: C, 71.09; H, 6.88; N, 3.60; Cl, 9.12. fnd: C, 71.63; H, 6.87; N, 3.50; Cl, 8.57.

20. (−)-cis-6-(4-Chloromethylphenyl)-8,9-dimethoxy-1,2,3,4,4a,10b-hexahydrophenanthridine EF: $C_{22}H_{24}ClNO_2$; MW: 369.9
$R_f$=0.6 (neutral silica gel, toluene:dioxane=2:1)

Optical rotation: $[\alpha]_D^{20}=-247.3°$ (c=0.2, ethanol)

21. (−)-cis-8,9-Dimethoxy-6-[4-(morpholin-4-ylmethyl)phenyl]-1,2,3,4,4a,10b-hexahydrophenanthridine 3.0 g of (−)-cis-6-(4-chloromethylphenyl)-8,9-dimethoxy-1,2,3,4,4a,10b-hexahydrophenanthridine (compound 20) and 2.2 g of potassium carbonate are suspended in 150 ml of dimethylformamide, treated with 1.1 g of morpholine and stirred at 50° C. for 3 h. The suspension is treated with water and extracted with diethyl ether. The organic phase is dried using sodium sulfate and concentrated. The residue is chromatographed on silica gel using petroleum ether (low)/ethyl acetate/triethylamine in the ratio 6/3/1.

EF: $C_{26}H_{32}N_2O_3$; MW: 420.56
Elemental analysis×0.4 $H_2O$: calc.: C, 73.00; H, 7.73; N, 6.55. fnd: C, 73.25; H, 7.69; N, 6.22.
Optical rotation: $[\alpha]_D^{20}=-73.5°$ (c=0.2, ethanol)

22. (−)-cis-8,9-Dimethoxy-6-[4-(4-methylpiperazin-1-ylmethyl)phenyl]-1,2,3,4,4a,10b-hexphenanthridine Prepared analogously to the preparation of example 21 starting also from (+)-cis-6-(4-chloromethylphenyl)-8,9-dimethoxy-1,2,3,4,4a,10b-hexahydrophenanthridine (compound 20).

EF: $C_{27}H_{35}N_3O_2$; MW: 433.60
$^1$H-NMR (200 MHz, DMSO-$d_6$): 1.1–1.95 ppm (m, 7H), 2.02–2.2 ppm (m, 1H), 2.15 ppm (s, 3H), 2.2–2.55 ppm (m, 8H), 2.57–2.78 ppm (m, 1H), 3.45–3.59 ppm (m, 1H), 3.52 ppm (s, 2H), 3.6 ppm (s, 3H), 3.84 ppm (s, 3H), 6.72 ppm (s, 1H), 6.98 ppm (s, 1H), 7.35–7.54 ppm (m, 4H)
Optical rotation: $[\alpha]_D^{20}=-66°$ (c=0.2, ethanol)

23. (−)-cis-8,9-Dimethoxy-6-[4-(3-methylbutyryl)phenyl]-1,2,3,4,4a,10b-hexahydrophenanthridine M. p. 114–117° C.
EF: $C_{26}H_{31}NO_3$; MW: 405.54
Elemental analysis: calc.:C, 77.01; H, 7.71; N, 3.45. fnd.: C, 76.90; H, 7.81; N, 3.41.
Optical rotation: $[\alpha]_D^{20}=-84.8°$ (c=0.2, ethanol)

24. (−)-cis-8,9-Dimethoxy-6-[4-cyclopropylmethylcarbonylphenyl]-1,2,3,4,4a,10b-hexahydrophenanthridine M. p. 93–98° C.
EF: $C_{26}H_{29}NO_3$; MW: 403.53
Elemental analysis: calc.:C, 77.39; H, 7.24; N, 3.47. fnd.: C, 76.99; H, 7.22; N, 3.34.
Optical rotation: $[\alpha]_D^{20}=-76.3°$ (c=0.2, ethanol)

25. (−)-cis-9-Ethoxy-8-methoxy-6-(4-benzoylphenyl)-1,2,3,4,4a,10b-hexahydrophenanthridine EF: $C_{29}H_{29}NO_3$; MW: 439.56
Elemental analysis: calc.:C, 79.24; H, 6.65; N, 3.19. fnd.: C, 78.94; H, 6.62; N, 3.19.
Optical rotation: $[\alpha]_D^{20}=-50°$ (c=0.2, ethanol)

26. (−)-cis-8,9-Dimethoxy-6-[4-(4-methoxybenzoyl)phenyl]-1,2,3,4,4a,10b-hexahydrophenanthridine EF: $C_{29}H_{29}NO_4$; MW: 455.56
Elemental analysis: calc.:C, 76.46; H, 6.42; N, 3.07. fnd.: C, 76.33; H, 6.55; N, 2.97.
Optical rotation: $[\alpha]_D^{20}=-61.7°$ (c=0.2, ethanol)

27. (−)-cis-8,9-Dimethoxy-6-[4-(4-chlorbenzoyl)phenyl]-1,2,3,4,4a,10b-hexahydrophenanthridine EF: $C_{28}H_{26}ClNO_3$; MW: 459.98
Elemental analysis×0.18 Toluene: calc.:C, 73.82; H, 5.82; N, 2.93; Cl, 7.41. fnd.: C 73.91; H, 5.89; N, 2.80 Cl 7.17
Optical rotation: $[\alpha]_D^{20}=-67.6°$ (c=0.2, ethanol)

28. (−)-cis-8,9-Dimethoxy-6-[4-(3-chlorbenzoyl)phenyl]-1,2,3,4,4a,10b-hexahydrophenanthridine M. p.180–183.5° C.
EF: $C_{28}H_{26}ClNO_3$; MW: 459.98
Elemental analysis: calc.:C, 73.11; H, 5.70; N, 3.04; Cl, 7.71. fnd.: C, 72.93; H, 5.76; N, 2.91; Cl, 7.84.
Optical rotation: $[\alpha]_D^{20}=-14.3°$ (c=0.2, ethanol)

29. (−)cis-8,9-Dimethoxy-6-[4-(4-nitrobenzoyl)phenyl]-1,2,3,4,4a,10b-hexahydrophenanthridine EF: $C_{28}H_{26}N_2O_5$; MW: 470.53
Elemental analysis×0.28 $H_2O$: calc.:C, 70.68; H, 5.63; N, 5.89. fnd.: C, 70.79; H, 5.85; N, 5.77.
Optical rotation: $[\alpha]_D^{20}=-65.1°$ (c=0.2, ethanol)

30. (−)-cis-8,9-Dimethoxy-6-[4-(3-methoxybenzoyl)phenyl]-1,2,3,4,4a,10b-hexahydrophenanthridine M. p. 146–148° C.
EF: $C_{29}H29NO_4$; MW: 455.56
Elemental analysis: calc.:C, 76.46; H, 6.42; N, 3.07. fnd.: C 76.53; H, 6.42; N, 3.00.
Optical rotation: $[\alpha]_D^{20}=-2.4°$ (c=0.1, ethanol)

31. (−)-cis-8,9-Dimethoxy-6-[4-(4-cyanobenzoyl)phenyl]-1,2,3,4,4a,10b-hexahydrophenanthridine EF: $C_{29}H_{26}N_2O_3$; MW: 450.54
Optical rotation: $[\alpha]_D^{20}56°$ (c=0.2, ethanol)

32. (−)-cis-8,9-Dimethoxy-6-[4-(pyridyl-4-carbonyl)phenyl]-1,2,3,4,4a,10b-hexahydrophenanthridine EF: $C_{27}H_{26}N_2O_3$; MW: 426.52
Elemental analysis×0.3 $H_2O$: calc.:C, 75.08; H, 6.21; N, 6.49. fnd.: C, 75.25; H, 6.32; N, 6.42.
Optical rotation: $[\alpha]_D^{20}=-72.9°$ (c=0.2, ethanol)

33. (−)-cis-8,9-Dimethoxy-6-[3-(phenylsulfonyl)phenyl]-1,2,3,4,4a,10b-hexahydrophenanthridine M. Bp.164–166° C.
EF: $C_{27}H_{27}NO_4S$; MW: 461.58
Elemental analysis×0.15 $H_2O$: calc.:C, 69.89; H, 5.92; N, 3.02; S, 6.91. fnd.: C, 69.75; H, 5.90; N, 3.22; S, 6.68.
Optical rotation: $[\alpha]_D^{20}106.3°$ (c=0.2, ethanol)

34. (−)-cis-8,9-Dimethoxy-6-[4-(phenylsulfonyl)phenyl]-1,2,3,4,4a,10b-hexahydrophenanthridine M. Bp.177–182° C.
EF: $C_{27}H_{27}NO_4S$; MW: 461.58
Elemental analysis: calc.:C, 70.26; H, 5.89; N, 3.03; S, 6.96. fnd.: C 70.23; H, 5.95; N, 2.89; S, 6.79.

Optical rotation: $[\alpha]_D^{20}=-91.5°$ (c=0.2, ethanol)

35. (−)-cis-8,9-Dimethoxy-6-(3-cyclopropylmethoxyphenyl)-1,2,3,4,4a,10b-hexahydrophenanthridine M. p. 54–61° C.

EF: $C_{25}H_{29}NO_3$; MW: 391.51

Elemental analysis: calc.:C, 76.70; H, 7.47; N, 3.58. fnd.: C, 76.67; H, 7.61; N, 3.56.

Optical rotation: $[\alpha]_D^{20}=-80°$ (c=0.2, ethanol)

36. (−)-cis-8,9-Dimethoxy-6-[3-(4-methoxyphenoxy)phenyl]-1,2,3,4,4a,10b-hexahydrophenanthridine

EF: $C_{28}H_{29}NO_4$; MW: 443.55

Elemental analysis: calc.:C, 75.82; H, 6.59; N, 3.16. fnd.: C, 75.76; H, 6.79; N, 3.25.

Optical rotation: $[\alpha]_D^{20}=-41.3°$ (c=0.2, ethanol)

37. (−)-cis-8,9-Dimethoxy-6-[3-(pyrid-4-yloxy)phenyl]-1,2,3,4,4a,10b-hexahydrophenanthridine

EF: $C_{26}H_{26}N_2O_3$; MW: 414.51

Elemental analysis×0.4 $H_2O$: calc.:C, 74.05; H, 6.41; N, 6.64. fnd.: C, 74.25; H, 6.36; N, 6.42.

Optical rotation: $[\alpha]_D^{20}=-35.2°$ (c=0.2, ethanol)

38. (−)-cis-8,9-Dimethoxy-6-(3-cyclopropylmethoxy-4-ethoxyphenyl)-1,2,3,4,4a,10b-hexahydrophenanthridine

EF: $C_{27}H_{33}NO_4$; MW: 435.57

Elemental analysis: calc.:C, 74.45; H, 7.64; N, 3.22. fnd.: C, 74.29; H, 7.67; N, 3.14.

Optical rotation: $[\alpha]_D^{20}=-87.8°$ (c=0.2, ethanol) 39. (−)-cis-9-Ethoxy-8-methoxy-6-[(3-cyclopropylmethoxy-4-ethoxy)phenyl]-1,2,3,4,4a,10b-hexahydrophenanthridine M. p. 102–105° C.

EF: $C_{26}H_{35}NO_4$; MW: 449.60

Elemental analysis: calc.:C, 74.80; H, 7.85; N, 3.12. fnd.: C, 74.82; H, 7.87; N, 3.05.

Optical rotation: $[\alpha]_D^{20}=-58.7°$ (c=0.2, ethanol)

40. (−)-cis-9-Ethoxy-8-methoxy-6-[3,4-bis(cyclopropylmethoxy)phenyl]-4,2,3,4,4a,10b-hexahydrophenanthridine

EF: $C_{30}H_{37}NO_4$; MW: 475.63

Elemental analysis: calc.:C, 75.76; H, 7.84; N, 2.94. fnd.: C, 75.66; H, 7.90; N, 3.01.

Optical rotation: $[\alpha]_D^{20}=-54.9°$ (c=0.2, ethanol)

41. (−)-cis8,9-Dimethoxy-6-[3,5-bis(cyclopropylmethoxy)phenyl]-1,2,3,4,4a,10b-hexahydrophenanthridine

EF: $C_{29}H_{35}NO_4$; MW: 461.61

Elemental analysis×0.17 $H_2O$: calc.:C, 74.96; H, 7.67; N, 3.01. fnd.: C, 74.99; H, 7.63; N, 2.97.

Optical rotation: $[\alpha]_D^{20}=-65.9°$ (c=0.2, ethanol)

42. (−)-cis-8,9-Dimethoxy-6-(3-cyclopropylmethoxy-4-difluoromethoxyphenyl)-1,2,3,4,4a,10b-hexahydrophenanthridine

EF: $C_{26}H_{29}F_2NO_4$; MW: 457.52

Elemental analysis: calc.:C, 68.26; H, 6.39; N, 3.06; F, 8.30. fnd.: C, 68.27; H, 6.45; N, 3.11; F, 8.25.

Optical rotation: $[\alpha]_D^{20}=-91.3°$ (c=0.2, ethanol)

43. (−)-cis-8,9-Dimethoxy-6-[3-(2-methoxyethoxy)-4-methoxyphenyl]-1,2,3,4,4a,10b-hexahydrophenanthridine

EF: $C_{25}H_{31}NO_5$; MW: 425.53

Elemental analysis: calc.:C, 70.57; H, 7.34; N, 3.29. fnd.: C, 70.35; H, 7.44; N, 3.25.

Optical rotation: $[\alpha]_D^{20}=-82.9°$ (c=0.2, ethanol)

44. (−)cis-8,9-Dimethoxy-6-[(3-cyclobutoxy-4-methoxy)phenyl]-1,2,3,4,4a,10b-hexahydrophenanthridine

EF: $C_{26}H_{31}NO_4$; MW: 421.54

Elemental analysis×0.17 $H_2O$: calc.:C, 73.55; H, 7.44; N, 3.30. fnd.: C, 73.36; H, 7.65; N, 3.40.

Optical rotation: $[\alpha]_D^{20}=-77.6°$ (c=0.2, ethanol)

45. (−)-cis-8,9-Dimethoxy-6-[(3-cyclopropylmethoxy-4-acetamido)phenyl]-1,2,3,4,4a,10b-hexahydrophenanthridine

EF: $C_{27}H_{32}N_2O_4$; MW: 448.57

Elemental analysis: calc.:C, 70.60; H, 7.29; N, 6.10. fnd.: C, 70.80; H, 7.35; N, 5.88.

Optical rotation: $[\alpha]_D^{20}=-80°$ (c=0.2, ethanol)

46. (−)-cis-8,9-Dimethoxy-6-[(4-methoxy-3-pyrrolidin-1-yl)phenyl]-1,2,3,4,4a,10b-hexahydrophenanthridine

EF: $C_{26}H_{32}N_2O_3$; MW: 420.56

Elemental analysis×0.23 $H_2O$: calc.:C, 73.51; H, 7.71; N, 6.59. fnd.: C, 73.75; H, 7.71; N, 6.35.

Optical rotation: $[\alpha]_D^{20}=-89.5°$ (c=0.2, ethanol)

47. (−)-cis-8,9-Dimethoxy-6-[4-methoxy-3-(2-oxopyrrolidin-1-yl)phenyl]-1,2,3,4,4a,10b-hexahydrophenanthridine M. p. 147–152° C.

EF: $C_{26}H_{30}N_2O_4$; MW: 434.54

Elemental analysis×0.39 $H_2O$: calc.:C, 70.71; H, 7.03; N, 6.34. fnd.: C, 70.82; H, 7.00; N, 6.23.

Optical rotation: $[\alpha]_D^{20}=-61.6°$ (c=0.2, ethanol)

48. (−)-cis-8,9-Dimethoxy-6-{[3-(2,5-dioxopyrrolidin-1-yl)-4-methoxy]phenyl}-1,2,3,4,4a,10b-hexahydrophenanthridine 2.5 g (−)-cis-8,9-Dimethoxy-6-[(3-amino-4-methoxy)phenyl]-1,2,3,4,4a,10b-hexahydrophenanthridine and 680 mg succinic acid anhydride are heated 14 h in a water trap. The solution is evaporated under reduced pressure and the residue is chromatographed on silica gel with toluene/dioxan/triethylamine in a ratio 10/1/1. After evaporation of the product containing fractions 0.28 g of the title compound with a m. p. 168–177° C. are obtained.

EF: $C_{26}H_{28}N_2O_5$; MW: 448.52

Elemental analysis: calc.:C, 69.63; H, 6.29; N, 6.25. fnd.: C, 69.29; H, 6.28; N, 6.17.

Optical rotation: $[\alpha]_D^{20}=-58.5°$ (c=0.2, ethanol)

49. (−)cis-8,9-Dimethoxy-6-(3-acetylphenyl)-1,2,3,4,4a,10b-hexahydrophenanthridine M. p. 112.5–114° C.

EF: $C_{23}H_{25}NO_3$; MW: 363.46

Elemental analysis: calc.:C, 76.01; H, 6.93; N, 3.85. fnd.: C, 75.62; H, 6.90; N, 3.83.

Optical rotation: $[\alpha]_D^{20}$=−168.7° (c=0.2, ethanol)

50. (−)-cis-8,9-Dimethoxy-6-[4-propionylphenyl]-1,2,3,4,4a,10b-hexahydrophenanthridine

EF: $C_{24}H_{27}NO_3$; MW: 377.49

Elemental analysis×0.24 $H_2O$: calc.:C, 75.50; H, 7.25; N, 3.67. fnd.: C, 75.52; H, 7.34; N, 3.55.

Optical rotation: $[\alpha]_D^{20}$=−71.3° (c=0.2, ethanol)

Starting Compounds

A1. (−)-cis-N-[2-(3,4-Dimethoxyphenyl)cyclohexyl]-4-benzoylbenzamide 4.0 g of (−)-cis-1,2-dimethoxy-4-(2-aminocyclohexyl)-benzene (compound B4) are dissolved in 40 ml of methylene chloride and 10.0 ml of triethylamine. A solution of 4.9 g of benzophenone-4-carbonyl chloride in 100 ml of methylene chloride is added dropwise at RT and the mixture is extracted, after stirring overnight, with 50 ml each of water, 2N hydrochloric acid, satd sodium hydrogencarbonate solution and water again. The organic phase is dried using sodium sulfate and concentrated. 7.78 g of the title compound are obtained as a crystallizing oil. M.p. 119–122.5° C.

Optical rotation: $[\alpha]_D^{20}$=−151.7° (c=0.2, ethanol)

Starting from the starting compounds described below, the following are obtained according to the procedure as in Example A1:

A2. (−)-cis-N-[2-(3,4-Dimethoxyphenyl)cyclohexyl]-4-acetobenzamide m.p. 129–137° C.

Optical rotation: $[\alpha]_D^{20}$=−180.4° (c=0.2, ethanol)

A3. (−)-cis-N-[2-(3,4-Dimethoxyphenyl)cyclohexyl]-3-benzoylbenzamide oil

Optical rotation: $[\alpha]_D^{20}$=−162.9° (c=0.2, ethanol)

A4. (−)-cis-N-[2-(3,4-Dimethoxyphenyl)cyclohexyl]-4-phenoxybenzamide m.p. 116–119.5° C.

Optical rotation: $[\alpha]_D^{20}$=−151.7° (c=0.2, ethanol)

A5. (−)-cis-N-[2-(3,4-Dimethoxyphenyl)cyclohexyl]-3-phenoxybenzamide oil

Optical rotation: $[\alpha]_D^{20}$=−97.1° (c=0.2, ethanol)

A6. (−)-cis-N-[2-(3,4-Dimethoxyphenyl)cyclohexyl]-3-phenylthiobenzamide m.p. 157.5–159.5° C.

Optical rotation: $[\alpha]_D^{20}$=−120.5° (c=0.2, ethanol)

A7. (−)-cis-N-[2-(3,4-Dimethoxyphenyl)cyclohexyl]-3-benzyloxybenzamide m.p. 131–133° C.

Optical rotation: $[\alpha]_D^{20}$=−108.8° (c=0.2, ethanol)

A8. (−)-cis-N-[2-(3,4-Dimethoxyphenyl)cyclohexyl]-3-(2-phenylethyloxy)benzamide solidifying oil Optical rotation: $[\alpha]_D^{20}$=−100.9° (c=0.2, ethanol)

A9. (−)-cis-N-[2-(3,4-Dimethoxyphenyl)cyclohexyl]-(3-cyclopentyloxy-4-methoxy)benzamide solidifying oil Optical rotation: $[\alpha]_D^{20}$=−117.3° (c=0.2, ethanol)

A10. (−)-cis-N-[2-(3,4-Dimethoxyphenyl)cyclohexyl]-(3-cyclopropylmethoxy-4-benzyloxy)benzamide m.p. 72.5–75.5° C.

Optical rotation: $[\alpha]_D^{20}$=−118° (c=0.2, ethanol)

A11. (−)-cis-N-[2-(3,4-Dimethoxyphenyl)cyclohexyl]-(3-benzyloxy-4-methoxy)benzamide m.p. 129.5–132° C.

Optical rotation: $[\alpha]_D^{20}$=−108° (c=0.2, ethanol)

A12. (−)-cis-N-[2-(3,4-Dimethoxyphenyl)cyclohexyl]-(3-cyclopropylmethoxy-4-methoxy)benzamide oil Optical rotation: $[\alpha]_D^{20}$=−133.2° (c=0.2, ethanol)

A13. (−)-cis-N-[2-(3,4-Dimethoxyphenyl)cyclohexyl]-3-methanesulfonyloxybenzamide m.p. 155–158° C.

Optical rotation: $[\alpha]_D^{20}$=−97.7° (c=0.2, ethanol)

A14. (−)-cis-N-[2-(3,4-Dimethoxyphenyl)cyclohexyl]-3-(p-toluenesulfonyloxy)benzamide solidifying oil Optical rotation: $[\alpha_D]^{20}$=−60° (c=0.2, ethanol)

A15. (−)-cis-N-[2-(3,4-Dimethoxyphenyl)cyclohexyl]-(3,4-bis-cyclopropylmethoxy)benzamide m.p. 90–98° C.

Optical rotation: $[\alpha]_D^{20}$=−119.1° (c=0.2, ethanol)

A16. (−)-cis-N-[2-(3,4-Dimethoxyphenyl)cyclohexyl]-4-(4-piperidinylcarbonyl)benzamide solidifying oil Optical rotation: $[\alpha]_D^{20}$=−128.3° (c=0.2, ethanol)

A17. (−)-cis-N-[2-(3,4-Dimethoxyphenyl)cyclohexyl]-4-(3-piperidinylcarbonyl)benzamide oil Optical rotation: $[\alpha]_D^{20}$=−88.6° (c=0.2, ethanol)

A18. (−)-cis-N-[2-(3,4-Dimethoxyphenyl)cyclohexyl]-4-methoxycarbonylmethylbenzamide m.p.: 88–98° C.

Optical rotation: $[\alpha]_D^{20}$=−116.2° (c=0.2, ethanol)

A19. cis-N-[2-(3-Ethoxy-4-methoxyphenyl)cyclohexyl]-4-chloromethylbenzamide m.p. 220–228° C.

A20. (−)-cis-N-[2-(3,4-Dimethoxyphenyl)cyclohexyl]-4-chloromethylbenzamide m.p. 94–97° C.

Optical rotation: $[\alpha]_D^{20}$=−150.2° (c=0.2, ethanol)

A21. (−)-cis-6-(4-Chloromethylphenyl)-8,9-dimethoxy-1,2,3,4,4a,10b-hexahydrophenanthridine Compare example 20.

A22. (−)-cis-6-(4-Chloromethylphenyl)-8,9-dimethoxy-1,2,3,4,4a,10b-hexahydrophenanthridine Compare example 20.

A23. (−)-cis-N-[2-(3,4-Dimethoxyphenyl)cyclohexyl]-4-(3-methylbutyryl)benzamide m.p. 118–120° C.
Optical Rotation: $[\alpha]_D^{20}=-168.2°$ (c=0.2 ethanol)

A24. (−)-cis-4-(2Cyclopropylmethylcarbonyl)-N-[2-(3,4-dimethoxyphenyl)cyclohexyl]benzamide solidifying oil
Optical Rotation: $[\alpha]_D^{20}=-151.4°$ (c0.2, ethanol)

A25. (−)-cis-N-2-(3-Ethoxy-4-methoxyphenyl)-cyclohexyl]-4-benzoylbenzamide solidifying oil
Optical Rotation: $[\alpha]_D^{20}=-151°$ (c=0.2, ethanol)

A26. (−)-cis-N-[2-(3,4-Dimethoxyphenyl)cyclohexyl]-4-(4-methoxybenzoyl)benzamide solidifying oil
Optical Rotation: $[\alpha]_D^{20}=-152.2°$ (c=0.2, ethanol)

A27. (−)-cis-4-[4-Chlorbenzoyl]-N-[2-(3,4-dimethoxyphenyl)cyclohexyl]benzamide m.p. 143–147.5° C.
Optical Rotation: $[\alpha]_D^{20}=-173.3°$ (c=0.2, ethanol)

A28. (−)-cis-4-[3-Chlorbenzoyl]-N-[2-(3,4-dimethoxyphenyl)cyclohexyl]benzamide solidifying oil
Optical Rotation: $[\alpha]_D^{20}=-146.8°$ (c=0.2, ethanol)

A29. (−)-cis-N-[2-(3,4-Dimethoxyphenyl)cyclohexyl]-4-[4-nitrobenzoyl]benzamide solidifying oil
Optical Rotation: $[\alpha]_D^{20}=-147.6°$ (c=0.2, ethanol)

A30. (−)-cis-N-[2-(3,4-Dimethoxyphenyl)cyclohexyl]-4-[3-methoxybenzoyl]benzamide solidifying oil
Optical Rotation $[\alpha]_D^{20}=-140.90°$ (c=0.2, ethanol)

A31. (−)-cis-4-[4-Cyanobenzoyl-N-[2-(3,4-dimethoxyphenyl)cyclohexyl]benzamide solidifying oil
Optical Rotation: $[\alpha]_D^{20}=-143.3°$ (c=0.2, ethanol)

A32. (−)-cis-N-2-(3,4-Dimethoxyphenyl)cyclohexyl]-4-(pyrid-4-ylcarbonyl)benzamide m.p. 109–117° C.
Optical Rotation: $[\alpha]_D^{20}=-193.7$(c=0.2, ethanol)

A33. (−)-cis-N-[2-(3,4-Dimethoxyphenyl)cyclohexyl]-3-phenylsulfonylbenzamide solidifying oil
Optical Rotation: $[\alpha]_D^{20}=-48.83°$ (c=0.2, ethanol)

A34. (−)-cis-N-[2-(3,4-Dimethoxyphenyl)cyclohexyl]-4-phenylsulfonylbenzamide

Optical Rotation: $[\alpha]_D^{20}=-134.1°$ (c=0.2, ethanol)

A35. (−)-cis-3-Cyclopropylmethoxy-N-[2-(3,4-dimethoxyphenyl)cyclohexyl]benzamide m.p. 84.5–96° C.
Optical Rotation: $[\alpha]_D^{20}=-95.5°$ (c=0.2, ethanol)

A36. (−)-cis-N-[2-(3,4-Dimethoxyphenyl)cyclohexyl]-3-(4-methoxyphenoxy)benzamide solidifying oil
Optical Rotation: $[\alpha]_D^{20}=-110.9°$ (c=0.2, ethanol)

A37. (−)-cis-N-[2-(3,4-Dimethoxyphenyl)cyclohexyl]-3-(pyrid-4-yloxy)benzamide m.p. 173–176° C.
Optical Rotation: $[\alpha]_D^{20}=-110.7°$ (c=0.2, ethanol)

A38. (−)-cis-3-Cyclopropylmethoxy-N-[2-(3,4-dimethoxyphenyl)cyclohexyl]-4-ethoxybenzamide m.p. 99–101° C.
Optical Rotation: $[\alpha]_D^{20}=-140.5°$ (c=0.2, ethanol)

A39. (−)-cis-3-Cyclopropylmethoxy-4-ethoxy-N-[-2-(3-ethoxy-4-methoxyphenyl)cyclohexyl]-benzamide m.p. 98–100° C.
Optical Rotation: $[\alpha]_D^{20}=-119.5°$ (c=0.2, ethanol)

A40. (−)-cis-3,4-Bis(cyclopropylmethoxy)-N-[2-(3-ethoxy-4-methoxyphenyl)cyclohexyl]-benzamide m.p. 91–98° C.
Optical Rotation: $[\alpha]_D^{20}=-107.1°$ (c=0.2, ethanol) A41. (−)-cis-3,5-Bis(cyclopropylmethoxy)-N-[2-(3,4-dimethoxyphenyl)cyclohexyl]benzamide solidifying oil
Optical Rotation: $[\alpha]_D^{20}=-71.6°$ (c=0.2, ethanol)

A42. -)-cis-3-Cyclopropylmethoxy-4-difluormethoxy-N-[2-(3,4-dimethoxyphenylucyclohexyl]-benzamide m.p. 90–91° C.
Optical Rotation: $[\alpha]_D^{20}=-92.5°$ (c=0.2, ethanol)

A43. (−)-cis-N-[2-(3,4-Dimethoxyphenyl)cyclohexyl]-4-methoxy-3-(2-methoxyethoxy)benzamide Optical Rotation: $[\alpha]_D^{20}=-130.2°$ (c=0.2, ethanol)

A44. (−)-cis-3-Cyclobutoxy-N-[2-(3,4-dimethoxyphenylicyclohexyl]-4-methoxybenzamide solidifying oil
Optical Rotation: $[\alpha]_D^{20}=-135.3°$ (c=0.2, ethanol)

A45. (−)-cis-4-Acetamido-3-cyclopropylmethoxy-N-[2-(3,4-dimethoxyphenyl)cyclohexyl]-benzamide solidifying oil
Optical Rotation: $[\alpha]_D^{20}=-153.3°$ (c=0.2, ethanol)

A46. (−)-cis-N-[2-(3,4-Dimethoxyphenyl)cyclohexyl]-4-methoxy-3-pyrrolidin-1-ylbenzamide solidifying oil
Optical Rotation: $[\alpha]_D^{20}=-125.1°$ (c=0.2, ethanol)

A47. (−)-cis-N-[2-(3,4-Dimethoxyphenyl) cyclohexyl]-4-methoxy-3-(2-oxopyrroldin-1-yl)-benzamide Optical Rotation: $[\alpha]_D^{20}=-113.5°$ (c=0.27 ethanol)

A48. (−)-cis-8,9-Dimethoxy-6-[(3-amino-4-methoxy)phenyl]-1,2,3,4,4a,10b-hexahydrophenanthridine Prepared from (−)-cis-N-[-2-(3,4-Dimethoxyphenyl) cyclohexyl]-4-methoxy-3-nitro-benzamide [optical rotation $[\alpha]_D^{20}=-119.1°$ (c=0.2, ethanol)] as described for compound 1.

EF: $C_{22}H_{24}N_2O_5$; MW: 396.45

Elemental analysis: calc.: C, 66.65; H, 6.10; N, 7.07. fnd.: C, 67.06; H, 6.21; N, 6.77.

Optical rotation: $[\alpha]_D^{20}=-137.5°$ (c=0.2, ethanol)

A49. (−)-cis-3-Acetyl-N-[2-(3,4-dimethoxyphenyl) cyclohexyl]benzamide solidifying oil Optical Rotation: $[\alpha]_D^{20}=-127.1°$ (c=0.2, ethanol)

A50. (−)-cis-N-[2-(3,4-Dimethoxyphenyl) cyclohexyl]-4-propionylbenzamide solidifying oil Optical Rotation: $[\alpha]_D^{20}=-160°$ (c=0.2, ethanol)

B1. (+/−)-cis-2-Ethoxy-1-methoxy-4-(2-aminocyclohexyl)benzene 40.0 g of (+/−)-cis-2-ethoxy-1-methoxy-4-(2-nitrocyclohex-4-enyl)benzene (compound C1) are dissolved in 1000 ml of ethanol and 500 ml of tetrahydrofuran, treated with 10 g of Raney nickel and hydrogenated in an autoclave for 4 days at a hydrogen pressure of 100 bar. After filtration and removal of the solvent in vacuo, 35.9 g of the title compound are obtained as a solidifying oil.

B2. (−)-cis-1-Methoxy-2-ethoxy-4-(2-aminocyclohexyl)benzene 65.0 g of (+/−)-cis-1-methoxy-2-ethoxy-4-(2-aminocyclohexyl)benzene and 100.0 g of (+)-O,O'-dibenzoyltartaric acid are dissolved in 900 ml of dioxane and 900 ml of methyl isobutyl ketone and the solution is stirred overnight at RT. The solid is filtered off with suction, washed by stirring 500 ml of acetone and 1000 ml of ethyl acetate, filtered off with suction again and dried. The product is treated with 600 ml of 2N sodium hydroxide solution and extracted with ethyl acetate. The organic phase is washed with water, dried using sodium sulfate and concentrated under reduced pressure. 15.3 g of the title compound are obtained as a pale yellow oil.

Optical rotation: $[\alpha]_D^{20}=-47.5°$ (c=0.2, ethanol).

B3. (+/−)-cis-1,2-Dimethoxy-4-(2-aminocyclohexyl)benzene 125 g of (+/−)-cis-1,2-dimethoxy-4-(2-nitrocyclohexyl) benzene and 120 g of zinc powder or granules are suspended in 1300 ml of ethanol. 220 ml of acetic acid are added dropwise at boiling heat. The precipitate is filtered off with suction and washed with ethanol, and the filtrate is concentrated under reduced pressure. The residue is taken up in hydrochloric acid and extracted with toluene. The aqueous phase is rendered alkaline using 50% strength sodium hydroxide solution, the precipitate is filtered off with suction and the filtrate is extracted with toluene. The organic phase is dried using sodium sulfate and concentrated. 98 g of the title compound are obtained as a crystallizing oil.

Alternatively 8.5 g of (+/−)-cis-1,2-dimethoxy-4-(2-nitrocyclohexyl) benzene are dissolved in 400 ml of methanol and treated at RT with 7 ml of hydrazine hydrate and 2.5 g of Raney nickel in portions in the course of 8 h. After stirring overnight at RT, the reaction mixture is filtered, the filtrate is concentrated and the residue is chromatographed on silica gel using a mixture of toluene/ethyl acetate/triethylamine=4/2/0.5. The title compound is obtained as an oil.

B4. (−)-cis-1,2-Dimethoxy-4-(2-aminocyclohexyl) benzene 12.0 g of (+/−)-cis-1,2-dimethoxy-4-(2-aminocyclohexyl) benzene and 6.2 g of (−)-mandelic acid are dissolved in 420 ml of dioxane and 60 ml of tetrahydrofuran and the solution is stirred overnight at RT. The solid is filtered off with suction, dried, treated with 100 ml of saturated sodium hydrogencarbonate solution and extracted with ethyl acetate. The organic phase is dried using sodium sulfate and concentrated under reduced pressure. 4.8 g of the title compound are obtained of m.p.: 80–81.5° C. Specific rotation: $[\alpha]_D^{20}=-58.5°$ C. (c=1, ethanol).

C1. (+/−)-cis-2-Ethoxy-1-methoxy-4-(2-nitrocyclohex-4-enyl)benzene 89.25 g of (+/−)-trans-2-ethoxy-1-methoxy-4-(2-nitrocyclohex-4-enyl)benzene (compound D1) and 37 g of potassium hydroxide are dissolved in 500 ml of absolute ethanol. A solution of 23.5 ml of conc. sulfuric acid in 120 ml of absolute ethanol is then added dropwise such that the internal temperature does not exceed −2° C. After stirring for 1 h, the mixture is added to 4 l of ice water, and the precipitate is filtered off with suction, washed with water and dried. M.p. 66–67° C.

C2. (+/−)-cis-1,2-Dimethoxy-4-(2-nitrocyclohex-4-enyl)benzene 10.0 g of (+/−)-trans-1,2-dimethoxy-4-(2-nitrocyclohex-4-enyl)benzene and 20.0 g of potassium hydroxide are dissolved in 150 ml of ethanol and 35 ml of dimethylformamide. A solution of 17.5 ml of conc. sulfuric acid in 60 ml of ethanol is then added dropwise such that the internal temperature does not exceed 4° C. After stirring for 1 h, the mixture is added to 1 l of ice water, the precipitate is filtered off with suction, washed with water and dried, and the crude product is recrystallized from ethanol. 8.6 g of the title compound of m.p. 82.5–84° C. are obtained.

C3. (+/−)-cis-1,2-Dimethoxy-4-(2-nitrocyclohexyl) benzene 8.4 g of (+/−)-cis-1,2-dimethoxy-4-(2-nitrocyclohex-4-enyl)benzene are dissolved in 450 ml of methanol, treated with 2 ml of conc. hydrochloric acid and hydrogenated after addition of 500 mg of 10% strength Pd/C. The reaction mixture is filtered and the filtrate is concentrated. M.p.: 84–86.5° C.

D1. (+/−)-trans-2-Ethoxy-1-methoxy-4-(2-nitrocyclohex-4-enyl)benzene 110 g of 3-ethoxy-2-methoxy-ω-nitrostyrene (compound E1) and 360 mg of hydroquinone are suspended in 360 ml of absolute toluene and treated with 180 ml of liquid 1,3-butadiene at −70° C. The mixture is stirred at 160–180° C. for 6 days in an autoclave and then cooled. The product is washed by stirring with ethanol, filtered off with suction and dried. M.p.: 130–131° C.

D2. (+/−)-trans-1,2-Dimethoxy-4-(2-nitrocyclohex-4-enyl)benzene 50.0 g of 3,4-dimethoxy-ω-nitrostyrene and, 1.0 g (9.1 mmol) of hydroquinone are suspended in 200 ml of abs. toluene and treated at −70° C. with 55.0 g (1.02 mol) of liquid 1,3-butadiene. The mixture is stirred at 160° C. for 6 days in an autoclave and then cooled. Some of the solvent is removed on a rotary evaporator, and the resulting precipitate is filtered off with suction and recrystallized in ethanol. M.p.: 113.5–115.5° C.

E1. 3-Ethoxy-2-methoxy-ω-nitrostyene 236 g of 3-ethoxy-2-methoxybenzaldehyde, 101 g of ammonium acetate and 320 ml of nitromethane are heated at 100° C. for 4 h in 655 ml of glacial acetic acid. The solution is added to 5 l of ice water, and the precipitate is filtered off with suction, washed with water and dried. M.p. 132–133° C.

E2. 3,4-Dimethoxy-ω-nitrostyrene 207.0 g of 3,4-dimethoxybenzaldehyde, 100.0 g of ammonium acetate and 125 ml of nitromethane are heated to boiling for 3–4 h in 1.0 l of glacial acetic acid. After cooling in an ice bath, the precipitate is filtered off with suction, rinsed with glacial acetic acid and petroleum ether and dried. M.p.: 140–141° C. Yield: 179.0 g.

Commercial Applicability

The compounds according to the invention have valuable pharmacological properties which make them commercially utilizable. As selective cyclic nucleotide phosphodiesterase (PDE) inhibitors (namely of type 4), they are suitable on the one hand as bronchial therapeutics (for the treatment of airway obstructions on account of their dilating but also on account of their respiratory rate- or respiratory drive-increasing action) and for the elimination of erectile dysfunction on account of the vasodilating action, but on the other hand especially for the treatment of disorders, in particular of inflammatory nature, e.g. of the airways (asthma prophylaxis), of the skin, of the central nervous system, of the intestine, of the eyes and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen radicals and proteases. The compounds according to the invention are distinguished here by low toxicity, good enteral absorption (high bioavailability), a large therapeutic breadth and the absence of significant side-effects.

On account of their PDE-inhibiting properties, the compounds according to the invention can be employed in human and veterinary medicine and therapeutics, where they can be used, for example, for the treatment and prophylaxis of the following illnesses: acute and chronic (in particular inflammatory and allergen-induced) airway disorders of various origins (bronchitis, allergic bronchitis, bronchial asthma, emphysema, COPD); dermatoses (especially of proliferative, inflammatory and allergic type) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and wide-area pyodermias, endogenous and exogenous acne, acne rosacea and other proliferative, inflammatory and allergic skin disorders; disorder which are based on an excessive release of TNF and leukotrienes, e.g. disorders of the arthritis type (rheumatoid arthritis, rheumatoid spondylitis, osteoarthritis and other arthritic conditions), disorders of the immune system (AIDS, multiple sclerosis), graft-versus-host reactions, transplant rejection reactions, symptoms of shock [septic shock, endotoxin shock, gram-negative sepsis, toxic shock syndrome and ARDS (adult respiratory distress syndrome)], and generalized inflammations in the gastrointestinal area (Crohn's disease and ulcerative colitis); disorders which are based on allergic and/or chronic, faulty immunological reactions in the area of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and the ureters in connection with kidney stones. In addition, the compounds according to the invention can be employed for the treatment of diabetes insipidus and disorders in connection with disturbances of brain metabolism, such as, for example, cerebral senility, senile dementia (Alzheimer's dementia), multiin-farct dementia or alternatively disorders of the CNS, such as, for example, depressions or arteriosclerotic dementia.

A further subject of the invention is a process for the treatment of mammals, including man, which are suffering from one of the abovementioned illnesses. The process comprises administering to the sick mammal a therapeutically efficacious and pharmacologically tolerable amount of one or more of the compounds according to the invention.

The invention further relates to the compounds according to the invention for use in the treatment of mammals, including man, which are suffering from one of the abovementioned illnesses. The process comprises administering to the sick mammal a therapeutically efficacious and pharmacologically tolerable amount of one or more of the compounds according to the invention.

The invention further relates to the compounds according to the invention for use in the treatment and/or prophylaxis of illnesses, in particular the illnesses mentioned.

The invention likewise relates to the use of the compounds according to the invention for the production of medicaments which are employed for the treatment and/or prophylaxis of the illnesses mentioned.

Medicaments for the treatment and/or prophylaxis of the illnesses mentioned, which contain one or more of the compounds according to the invention, are furthermore a subject of the invention.

A further subject of the invention is a commercial product, consisting of a customary secondary pack, a primary pack containing the medicament (for example an ampoule or a blister pack) and, optionally, a pack insert, the medicament exhibiting antagonistic action against cyclic nucleotide phosphodiesterases of type 4 (PDE4) and leading to the attenuation of the symptoms of illnesses which are connected with cyclic nucleotide phosphodiesterases of type 4, and the suitability of the medicament for the prophylaxis or treatment of illnesses which are connected with cyclic nucleotide phosphodiesterases of the type 4 being indicated on the secondary pack and/or on the pack insert of the commercial product, and the medicament containing one or more compounds of the formula I according to the invention. The secondary pack, the primary pack containing the medicament and the pack insert otherwise comply with what would be regarded as standard to the person skilled in the art for medicaments of this type.

The medicaments are prepared by processes which are known per se and familiar to the person skilled in the art. As medicaments, the compounds according to the invention (=active compounds) are either employed as such, or preferably in combination with suitable pharmaceutical excipients, e.g. in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this, these are either administered directly as a powder (preferably in micronized form) or by nebulization of solutions or suspensions which contain them. With respect to the preparations and administration forms, reference is made, for example, to the details in European Patent 163 965.

For the treatment of dermatoses, the compounds according to the invention are in particular used in the form of those medicaments which are suitable for topical application. For the production of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. Dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg per kilogram per day.

Biological Investigations

In the investigation of PDE4 inhibition at the cellular level, the activation of inflammatory cells has particular importance. As an example, the FMLP (N-formyl-methionyl-leucyl-phenylalanine)-induced superoxide production of neutrophilic granulocytes may be mentioned, which can be measured as luminol-potentiated chemoluminescence [McPhail L C, Strum S L, Leone P A and Sozzani S, The neutrophil respiratory burst mechanism. In "Immunology Series" 1992, 57, 47–76; ed. Coffey R G (Marcel Decker, Inc. New York-Basle-Hong Kong)].

Substances which inhibit chemoluminescence and cytokine secretion and the secretion of inflammatory mediators on inflammatory cells, in particular neutrophilic and eosinophilic granulocytes, T lymphocytes, monocytes and macrophages, are those which inhibit PDE4. This isoenzyme of the phosphodiesterase families is particularly represented in granulocytes. Its inhibition leads to an increase in the intracellular cyclic AMP concentration and thus to the inhibition of cell activation. PDE4 inhibition by the substances according to the invention is thus a central indicator of the suppression of inflammatory processes (Glembycz MA, Could isoenzyme-selective phosphodiesterase inhibitors render bronchodilatory therapy redundant in the treatment of bronchial asthma?. Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE 3/4 inhibitor. In "New Drugs for Asthma Therapy", 379–402, Birkhäuser Verlag Basle 1991; Schudt C et al., Influence of selective phosphodiesterase inhibitors on human neutrophil functions and levels of cAMP and Ca; Naunyn-Schmiedebergs Arch Pharmacol 1991, 344, 682–690; Tenor H and Schudt C, Analysis of PDE isoenzyme profiles in cells and tissues by pharmacological methods. In "Phosphodiesterase Inhibitors", 21–40, "The Handbook of Immunopharmacology", Academic Press, 1996; Hatzelmann A et al., Enzymatic and functional aspects of dual-selective. PDE3/4-inhibitors. In "Phosphodiesterase Inhibitors", 147–160. "The Handbook of Immunopharmacology", Academic Press, 1996).

Inhibition of PDE4 Activity

Methodology

The activity test was carried out according to the method of Bauer and Schwabe, which was adapted to microtiter plates (Naunyn-Schmiedeberg's Arch. Pharmacol. 1980, 311, 193–198). The PDE reaction takes place in the first step here. In a second step, the resulting 5'-nucleotide is cleaved by a 5'-nucleotidase of the snake venom of Crotalus atrox to the uncharged nucleoside. In the third step, the nucleoside is separated from the remaining charged substrate on ion-exchange columns. The columns are eluted directly into minivials, into which 2 ml of scintillator fluid are additionally added, for counting using 2 ml of 30 mM ammonium formate (pH 6.0).

The inhibitory values determined for the compounds according to the invention [inhibitory concentration as $-\log \mathrm{Ic}_{50}$ (mol/l)] follow from the following Table A, in which the numbers of the compounds correspond to the numbers of the examples.

TABLE A

Inhibition of the PDE4 activity

| Compound | $-\log \mathrm{IC}_{50}$ |
| --- | --- |
| 1 | 7.82 |
| 2 | 7.27 |
| 3 | 8.64 |
| 4 | 7.52 |
| 5 | 8.54 |
| 7 | 8.40 |
| 8 | 8.41 |
| 9 | 7.79 |
| 10 | 8.09 |
| 11 | 8.03 |
| 12 | 7.80 |
| 13 | 8.33 |

TABLE A-continued

Inhibition of the PDE4 activity

| Compound | −log IC$_{50}$ |
| --- | --- |
| 14 | 8.44 |
| 15 | 7.89 |
| 16 | 8.02 |
| 17 | 8.13 |
| 18 | 7.49 |
| 19 | 8.59 |
| 21 | 7.35 |
| 22 | 7.27 |
| 23 | 7.5 |
| 24 | 7.48 |
| 25 | 8.87 |
| 26 | 7.46 |
| 27 | 7.3 |
| 28 | 7.61 |
| 29 | 7.28 |
| 30 | 7.94 |
| 31 | 7.8 |
| 32 | 7.45 |
| 33 | 8.23 |
| 34 | 7.89 |
| 35 | 7.43 |
| 36 | 8.78 |
| 37 | 7.92 |
| 38 | 7.47 |
| 39 | 8.87 |
| 40 | 8.65 |
| 41 | 8.03 |
| 42 | 7.43 |
| 44 | 7.58 |
| 45 | 8.04 |
| 46 | 7.16 |
| 47 | 7.33 |
| 48 | 7.67 |
| 49 | 7.17 |
| 50 | 7.98 |

I claim:

1. A compound of formula I,

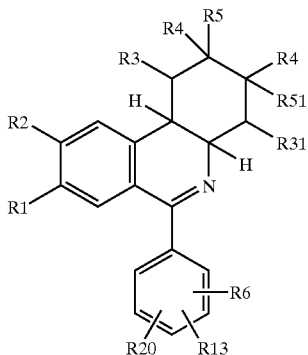

(I)

in which
R1 is hydroxyl, 1–4C-alkoxy, 3–7C-cycloalkoxy, 3–7C-cycloalkylmethoxy or completely or predominantly fluorine-substituted 1–4C-alkoxy,
R2 is hydroxyl, 1–4C-alkoxy, 3–7C-cycloalkoxy, 3–7C-cycloalkylmethoxy or completely or predominantly fluorine-substituted 1–4C-alkoxy,
or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–4C-alkyl,
R5 is hydrogen,
R51 is hydrogen,
or in which
R5 and R51 together represent an additional bond,
R6 is O-R7, S—R8, C(O)—R9, CH$_2$—R10, S(O)$_2$-aryl, O—S(O)$_2$—R11, pyrrolidin-1-yl, pyrrolidin-1-yl-2-one, pyrrolidin-1-yl-2,5-dione, piperidin-1-yl, piperidin-1-yl-2-one or piperidin-1-yl-2,6-dione, where
R7 is 3–7C-cycloalkyl, 3–7C-cycloalkylmethyl, 1–4C-alkoxy-1-4C-alkyl, aryl or phenyl-1–4C-alkyl,
R8 is hydrogen, 1–4C-alkyl, 1–4C-alkylcarbonyl, arylcarbonyl, trifluoromethyl, difluoromethyl, trichloromethyl or phenyl,
R9 is 1–4C-alkyl, 3–7C-cycloalkyl, 3–7C-cycloalkylmethyl, 1-pyrrolidinyl, 1-piperidinyl, 1-piperazinyl, 4-methylpiperazinyl, 4-morpholinyl or aryl,
R10 is hydroxyl, halogen, cyano, carboxyl, 1–4C-alkoxy, phenoxy, 1–4C-alkoxycarbonyl, aminocarbonyl, mono- or di-1–4C-alkylaminocarbonyl, N(R15)R16 or 1–4C-alkylcarbonylamino, and
R11 is 1–4C-alkyl, amino, mono- or di-1–4C-alkylamino or aryl, aryl is phenyl, pyridyl or R12-substituted phenyl, where
R12 is hydroxyl, halogen, carboxyl, nitro, amino, cyano, 1–4C-alkyl, trifluoromethyl, 1–4C-alkoxy, 1–4C-alkoxycarbonyl, 1–4C-alkylcarbonylamino, 1–4C-alkylcarbonyloxy or aminocarbonyl,
R13 is hydrogen, hydroxyl, halogen, cyano, nitro, amino, 1–4C-alkyl, trifluoromethyl, 1–4C-alkoxy, completely or predominantly fluorine-substituted 1–4C-alkoxy, phenyl, phenyl-1–4C-alkyl, C(O)—OR14, C(O)—N(R15)R16, N(R17)R18, S(O)$_2$—R19, S(O)$_2$—N(R15)R16 or has one of the meanings of R6, where
R14 is hydrogen, 1–4C-alkyl, 3–7C-cycloalkyl or 3–7C-cycloalkylmethyl,
R15 is hydrogen, 1–4C-alkyl, 3–7C-cycloalkyl or 3–7C-cycloalkylmethyl,
R16 is hydrogen, 1–4C-alkyl, 3–7C-cycloalkyl, 3–7C-cycloalkylmethyl or aryl,
or where R15 and R16, together and including the nitrogen atom to which both are bonded, represent a 1-pyrrolidinyl, 1-piperidinyl, 1-piperazinyl, 4-methylpiperazin-1-yl, 1-hexahydroazepinyl or 4-morpholinyl radical,
R17 is hydrogen, 1–4C-alkyl, S(O)$_2$—R19 or S(O)$_2$-aryl,
R18 is 1–4C-alkyl, 1–4C-alkylcarbonyl, 3–7C-cycloalkylcarbonyl, 3–7C-cycloalkylmethylcarbonyl, S(O)$_2$—R19 or S(O)$_2$-aryl, and
R19 is 1–4C-alkyl,
R20 is hydrogen, hydroxyl, halogen, nitro, amino, 1–4C-alkyl, trifluoromethyl, 1–4C-alkoxy, completely or predominantly fluorine-substituted 1–4C-alkoxy, 3–7C-cycloalkoxy, 3–7C-cycloalkylmethoxy, CH$_2$—R10, carboxyl, 1–4C-alkoxycarbonyl, 1–4C-alkylcarbonyloxy, 1–4C-alkylcarbonylamino or aminocarbonyl,
or a pharmaceutically acceptable salt, an N-oxide, or a salt of an N-oxide of this compound.

2. A compound of formula I as claimed in claim 1, in which
R1 is 1–2C-alkoxy, 3–5C-cycloalkoxy, 3–5C-cycloalkylmethoxy or completely or predominantly fluorine-substituted 1–2C-alkoxy, R2 is 1–2C-alkoxy, 3–5C-cycloalkoxy, 3–5C-cycloalkylmethoxy or completely or predominantly fluorine-substituted 1–2C-alkoxy, R3 is hydrogen, R31 is hydrogen, R4 is hydrogen or 1–2C-alkyl, R5 is hydrogen, R51 is hydrogen, or in which R5 and R51 together represent an additional bond, R6 is O—R7, S—R8, C(O)—R9, CH$_2$—R10, SO$_2$-aryl, O—S(O)$_2$—R11, pyrrolidin-1-yl, pyrrolidin-1-yl-2-one or pyrrolidin-1-yl-2,5-dione, where R7 is 3–7C-cycloalkyl, 3–7C-cycloalkylmethyl, 1–4C-alkoxy-1–4C-alkyl, aryl or phenyl-1–4C-alkyl, R8 is hydrogen, 1–4C-alkyl, acetyl, phenylcarbonyl, trifluoromethyl or phenyl, R9 is 1–4C-alkyl, 3–7C-cycloalkyl, 3–7C-cycloalkylmethyl, 1-piperidinyl, 1-piperazinyl, 4-methylpiperazinyl, 4-morpholinyl or aryl, R10 is halogen, carboxyl, 1–4C-alkoxy, phenoxy, 1–4C-alkoxycarbonyl, aminocarbonyl, mono- or di-1–4C-alkylaminocarbonyl, N(R15)R16 or 1–4C-alkylcarbonylamino, and R11 is 1–4C-alkyl, mono- or di-1–4C-alkylamino or aryl, aryl is phenyl, pyridyl or R12-substituted phenyl, where R12 is halogen, carboxyl, nitro, amino, cyano, 1–4C-alkyl, trifluoromethyl or 1–4C-alkoxy, R13 is hydrogen, hydroxyl, halogen, cyano, nitro, amino, 1–4C-alkyl, trifluoromethyl, 1–4C-alkoxy, completely or predominantly fluorine-substituted 1–4C-alkoxy, phenyl, phenyl-1–4C-alkyl, C(O)—OR14, C(O)—N(R15)R16, N(R17)R18, S(O)$_2$—R19, S(O)$_2$—N(R15)R16 or has one of the meanings of R6, where R14 is hydrogen or 1–4C-alkyl, R15 is hydrogen or 1–4C-alkyl, R16 is hydrogen, 1–4C-alkyl or aryl, or where R15 and R16, together and including the nitrogen atom to which both are bonded, are a 1-piperidyl, 1-piperazinyl, 1-methylpiperazin-4-yl or 4-morpholinyl radical, R17 is hydrogen, 1–4C-alkyl, S(O)$_2$—R19 or S(O)$_2$-aryl, R18 is 1–4C-alkyl, 1–4C-alkylcarbonyl, 3–7C-cycloalkylcarbonyl, 3–7C-cycloalkylmethylcarbonyl, S(O)$_2$—R19 or S(O)$_2$-aryl, and R19 is 1–4C-alkyl, R20 is hydrogen, hydroxyl, halogen, nitro, amino, 1–4C-alkyl, trifluoromethyl, 1–4C-alkoxy, completely or predominantly fluorine-substituted 1–4C-alkoxy, 3–7C-cycloalkoxy, 3–7C-cycloalkyl-methoxy, carboxyl, 1–4C-alkoxycarbonyl or 1–4C-alkylcarbonyloxy, or a pharmaceutically acceptable salt, an N-oxide, or a salt of an N-oxide of this compound.

3. A compound of formula I as claimed in claim 1, in which

R1 is 1–2C-alkoxy,

R2 is 1–2C-alkoxy,

R3, R31, R4, R5 and R51 are hydrogen,

R6 is O—R7, S—R8, C(O)—R9, CH$_2$—R10, S(O)$_2$-phenyl, O—S(O)$_2$—R11, pyrrolidin-1-yl, pyrrolidin-1-yl-2-one or pyrrolidin-1-yl-2,5-dione, where R7 is 3–5C-cycloalkyl, 3–5C-cycloalkylmethyl, 1–2C-alkoxy-1–2C-alkyl, aryl or phenyl-1–2C-alkyl, R8 is phenyl, R9 is 1–4C-alkyl, 3–5C-cycloalkylmethyl, 1-piperidinyl or aryl, R10 is halogen, 1–4C-alkoxycarbonyl or N(R15)R16, and R11 is methyl or 4-methylphenyl, aryl is phenyl, pyridyl or R12-substituted phenyl, where R12 is 1–4C-alkyl, 1–4C-alkoxy, halogen, nitro or cyano, R15 is 1–4C-alkyl, and R16 is 1–4C-alkyl, or where R15 and R16, together and including the nitrogen atom to which both are bonded, are a 1-piperidinyl, 1-piperazinyl, 1-methylpiperazin-4-yl or 4-morpholinyl radical, and in which either R13 is hydrogen, 1–4C-alkoxy, completely or predominantly fluorine-substituted 1–2C-alkoxy, or 1–4C-alkylcarbonylamino and R20 is hydrogen, or R13 is hydrogen and R20 is 3–5C-cycloalkoxy or 3–5C-cycloalkylmethoxy, or a pharmaceutically acceptable salt, an N-oxide, or a salt of an N-oxide of this compound.

4. A compound of formula I as claimed in claim 1, in which

R1 is 1–2C-alkoxy,

R2 is 1–2C-alkoxy,

R3, R31, R4, R5 and R51 are hydrogen,

R6 is O—R7, S—R8, C(O)—R9, CH$_2$—R10, S(O)$_2$-phenyl, O—S(O)$_2$—R11, pyrrolidin-1-yl or pyrrolidin-1-yl-2-one, where R7 is cyclobutyl, cyclopentyl, cyclopropylmethyl, 2-methoxyethyl, phenyl, 4-methoxyphenyl, benzyl, phenethyl or pyridyl, R8 is phenyl, R9 is methyl, ethyl, isobutyl, cyclopropylmethyl, 1-piperidinyl or aryl, R10 is methoxycarbonyl, morpholin-4-yl or 1-methylpiperazin-4-yl, and R11 is methyl or 4-methylphenyl, aryl is phenyl, pyridyl or R12-substituted phenyl, in which R12 is methoxy, halogen, nitro or cyano, and in which either R13 is hydrogen, methoxy, ethoxy, difluoromethoxy or acetylamino and R20 is hydrogen, or R13 is hydrogen and R20 is cyclopropylmethoxy, or a pharmaceutically acceptable salt, an N-oxide, or a salt of an N-oxide of this compound.

5. A compound of formula I as claimed in claim 1, in which

R1 is hydroxyl, 1–4C-alkoxy, 3–7C-cycloalkoxy, 3–7C-cycloalkylmethoxy or completely or predominantly fluorine-substituted 1–4C-alkoxy, R2 is hydroxyl, 1–4C-alkoxy, 3–7C-cycloalkoxy, 3–7C-cycloalkylmethoxy or completely or predominantly fluorine-substituted 1–4C-alkoxy, or in which R1 and R2 together are a 1–2C-alkylenedioxy group, R3 is hydrogen or 1–4C-alkyl, R31 is hydrogen or 1–4C-alkyl,
or in which
R3 and R31 together are a 1–4C-alkylene group,
R4 is hydrogen or 1–4C-alkyl,
R5 is hydrogen,
R51 is hydrogen,
or in which
R5 and R51 together are an additional bond,
R6 is O—R7, S—R8, C(O)—R9, $CH_2$—R10 or O—S$(O)_2$—R11, where
R7 is 3–7C-cycloalkyl, 3–7C-cycloalkylmethyl, aryl or phenyl-1–4C-alkyl,
R8 is hydrogen, 1–4C-alkyl, 1–4C-alkylcarbonyl, trifluoromethyl, difluoromethyl, trichloromethyl or phenyl,
R9 is 1–4C-alkyl, 1-pyrrolidinyl, 1-piperidinyl, 1-piperazinyl, 4-methylpiperazinyl, 4-morpholinyl or aryl,
R10 is hydroxyl, halogen, cyano, carboxyl, 1–4C-alkoxy, phenoxy, 1–4C-alkoxycarbonyl, aminocarbonyl, mono- or di-1–4C-alkylaminocarbonyl, N(R15)R16 or 1–4C-alkylcarbonylamino, and
R11 is 1–4C-alkyl, amino, mono- or di-1–4C-alkylamino or aryl,
aryl is phenyl, pyridyl or R12-substituted phenyl, where
R12 is hydroxyl, halogen, carboxyl, nitro, amino, cyano, 1–4C-alkyl, trifluoromethyl, 1–4C-alkoxy, 1–4C-alkoxycarbonyl, 1–4C-alkylcarbonylamino, 1–4C-alkylcarbonyloxy or aminocarbonyl,
R13 is hydrogen, hydroxyl, halogen, cyano, nitro, amino, 1–4C-alkyl, trifluoromethyl, 1–4C-alkoxy, completely or predominantly fluorine-substituted 1–4C-alkoxy, phenyl, phenyl-1–4C-alkyl, C(O)—OR14, C(O)—N(R15)R16, N(R17)R18, $S(O)_2$-R19, $S(O)_2$—N(R15)R16 or has one of the meanings of R6, where
R14 is hydrogen, 1–4C-alkyl, 3–7C-cycloalkyl or 3–7C-cycloalkylmethyl,
R15 is hydrogen, 1–4C-alkyl, 3–7C-cycloalkyl or 3–7C-cycloalkylmethyl,
R16 is hydrogen, 1–4C-alkyl, 3–7C-cycloalkyl, 3–7C-cycloalkylmethyl or aryl,
or where R15 and R16, together and including the nitrogen atom to which both are bonded, are a 1-pyrrolidinyl, 1-piperidinyl, 1-piperazinyl, 4-methylpiperazin-1-yl, 1-hexahydroazepinyl or 4-morpholinyl radical,
R17 is hydrogen, 1–4C-alkyl, $S(O)_2$—R19 or $S(O)_2$-aryl,
R18 is 1–4C-alkyl, 1–4C-alkylcarbonyl or $S(O)_2$—R19 or $S(O)_2$-aryl, and R19 is 1–4C-alkyl,
R20 is hydrogen, hydroxyl, halogen, nitro, amino, 1–4C-alkyl, trifluoromethyl, 1–4C-alkoxy, completely or predominantly fluorine-substituted 1–4C-alkoxy, 3–7C-cycloalkoxy, 3–7C-cycloalkylmethoxy, $CH_2$—R10, carboxyl, 1–4C-alkoxycarbonyl, 1–4C-alkylcarbonyloxy, 1–4C-alkylcarbonylamino or aminocarbonyl,
or a pharmaceutically acceptable salt, an N-oxide, or a salt of an N-oxide of this compound.

6. A compound of formula I as claimed in claim 1, in which
R1 is 1–2C-alkoxy,
R2 is 1–2C-alkoxy,
R3, R31, R4, R5 and R51 are hydrogen,
R6 is O—R7, S—R8, C(O)—R9, $CH_2$—R10 or O—S$(O)_2$—R11, where
R7 is cyclopentyl, cyclopropylmethyl, phenyl, benzyl or phenethyl,
R8 is phenyl,
R9 is methyl, 1-piperidinyl or phenyl,
R10 is halogen, methoxycarbonyl, morpholin-4-yl or 1-methylpiperazin-4-yl and
R11 is methyl or 4-methylphenyl,
and in which either
R13 is hydrogen or methoxy and
R20 is hydrogen, or
R13 is hydrogen and
R20 is cyclopropylmethoxy
or a pharmaceutically acceptable salt, an N-oxide, or a salt of an N-oxide of this compound.

7. A compound of formula I as claimed in claim 1, which has the same absolute configuration in positions 4a and 10b as the compound (−)-cis-1,2-dimethoxy-4-(2-aminocyclohexyl)benzene having the optical rotation $[\alpha]^{20}=-58.5°$ (c=1, ethanol), which is used as a starting material.

8. A method for treating an illness treatable by administration of a PDE IV inhibitor in a patient comprising administering to said patient in need thereof a PDE IV inhibiting amount of the compound of formula I as claimed in claim 1.

9. A pharmaceutical composition comprising at least one compound of formula I as claimed in claim 1 together with pharmaceutically acceptable excipients and/or vehicles.

10. A method for treating an airway disorder in a patient comprising administering to said patient in need thereof a therapeutically effective amount of the compound of formula I as claimed in claim 1.

* * * * *

UNITED STATES PATENT AND TRADEMARK OFFICE
CERTIFICATE OF CORRECTION

PATENT NO. : 6,476,025 B2
DATED : November 5, 2002
INVENTOR(S) : Beate Gutterer

Page 1 of 1

It is certified that error appears in the above-identified patent and that said Letters Patent is hereby corrected as shown below:

Column 34,
Lines 24-26, please replace with the following:
-- R11 is 1-4C-alkyl, amino, mono- or di-1-4C-alkylamino
　　　or aryl,
aryl is phenyl, pyridyl or R12-substituted phenyl, where --

Column 35,
Lines 27-29, please replace with the following:
-- R11 is 1-4C-alkyl, amino, mono- or di-1-4C-alkylamino or aryl,
aryl is phenyl, pyridyl or R12-substituted phenyl,
　　　where --

Signed and Sealed this

Fourth Day of February, 2003

JAMES E. ROGAN
*Director of the United States Patent and Trademark Office*